(12) United States Patent
King

(10) Patent No.: US 11,523,941 B2
(45) Date of Patent: Dec. 13, 2022

(54) DEVICES FOR APPLICATION OF LOCALIZED HYPOTHERMIC THERAPY TO THE HUMAN EAR

(71) Applicant: Restorear, LLC, Kirkland, WA (US)

(72) Inventor: Curtis S. King, Kirkland, WA (US)

(*) Notice: Subject to any disclaimer, the term of this patent is extended or adjusted under 35 U.S.C. 154(b) by 1088 days.

(21) Appl. No.: 16/163,479

(22) Filed: Oct. 17, 2018

(65) Prior Publication Data
US 2019/0110931 A1     Apr. 18, 2019

Related U.S. Application Data

(60) Provisional application No. 62/573,716, filed on Oct. 18, 2017.

(51) Int. Cl.
*A61F 11/14*     (2006.01)
*A61F 7/10*      (2006.01)
(Continued)

(52) U.S. Cl.
CPC .............. *A61F 11/14* (2013.01); *A61F 7/007* (2013.01); *A61F 7/02* (2013.01); *A61F 7/10* (2013.01); *A61F 7/12* (2013.01); *A61F 2007/0005* (2013.01); *A61F 2007/0075* (2013.01); *A61F 2007/108* (2013.01)

(58) Field of Classification Search
CPC ....... A61F 11/14; A61F 7/10; A61F 2007/005
See application file for complete search history.

(56) References Cited

U.S. PATENT DOCUMENTS

| 4,190,054 A | * | 2/1980 | Brennan | ................... A61F 7/02 607/109 |
| 5,456,703 A | * | 10/1995 | Beeuwkes, III | ......... A61F 7/02 607/109 |

(Continued)

FOREIGN PATENT DOCUMENTS

JP     2006230761 A  *  9/2006

OTHER PUBLICATIONS

Machine Translation of JP2006230761 A to Fumino Yuyaka (Year: 2006).*

*Primary Examiner* — Kaitlyn E Smith
(74) *Attorney, Agent, or Firm* — Brian C. Trask

(57) ABSTRACT

A heat transfer device particularly structured for application of thermal therapy from a contact surface to a human ear. A device may be passive (pre-cooled), active (thermoelectrically active), or include elements of both. A device may be structured to apply thermal treatment from a contact surface of a contact cavity only to a localized posterior area relative to the circumference of an ear. Preferably, a device provides an uninterrupted opening extending in a line-of-sight between an ear canal and the local environment. A device may include both of a contact cavity and a bulk cavity, with heat transfer media disposed in each cavity. Typically, a bulk cavity holds at least twice the media volume contained in a contact cavity. The cavities may be disposed in fluid communication, or separated by a barrier to permit only thermal communication there-between. When a barrier is present, a device may include different heat transfer media in each cavity. One or more device may be associated with various mounting structure to dispose a contact surface in contact with desired portion(s) of a head.

11 Claims, 35 Drawing Sheets

(51) Int. Cl.
*A61F 7/02* (2006.01)
*A61F 7/00* (2006.01)
*A61F 7/12* (2006.01)

(56) References Cited

U.S. PATENT DOCUMENTS 7,335,222 B1 2/2008 Tyler
2016/0323664 A1* 11/2016 Kirsch .................... A61F 11/14

* cited by examiner

DEVICES FOR APPLICATION OF LOCALIZED HYPOTHERMIC THERAPY TO THE HUMAN EAR

RELATED APPLICATIONS

This application claims the benefit under 35 U.S.C. 119(e) of the filing date of Provisional Application Ser. No. 62/573,716, filed Oct. 18, 2017, for "Devices and Methods for Application of Localized Hypothermic Therapy to the Human Ear".

BACKGROUND

Field of the Invention

This invention relates to devices and methods for hypothermic therapy. It is particularly directed to devices and methods for application of hypothermic therapy to a human ear.

State of the Art

It has long been known that application of hypothermic therapy (i.e., "therapeutic cooling") of human body tissue can be beneficial in reducing inflammation and limiting adverse effects related to injury. Cooling therapy using e.g., ice, ice-packs, etc., has been used for centuries to treat injury. This trend continues today, and cooling therapy remains the first line of treatment for a variety of injuries. Consumer devices with different types of materials (gels, various polymeric fluids, etc.) are commercially available, and are commonly used. These devices are often designed with specific geometry or features such that the device, when installed on the human body, can efficiently cool the injured area, and reduce the severity of the inflammatory response.

In some instances, modern techniques utilizing therapeutic hypothermia have been developed, and have now become standard of care for advanced medical cases. It is commonly known that for patients suffering cardiac arrest, lowering the body temperature as quickly as possible after trauma offers significant benefits. In cases of traumatic central nervous system injuries (brain and spinal cord), localized hypothermic therapy (in these cases, referred to as Targeted Temperature Management) also shows promising results as a method for improved outcomes.

Most recently, work in the field of otolaryngology and audiology has shown that there is a potential benefit to the use of this targeted/localized therapeutic hypothermia for the treatment of noise induced hearing loss, or hearing damage. Animal studies have shown that the application of localized cooling to the external regions of the skull nearest the ears (specifically, areas of the skull nearest the organs/structures of the outer, middle, and inner ear), following noise trauma may reduce or eliminate hearing damage. Data shows that application of this therapy may offer significant benefits for reducing hearing damage in both the long and the short term. Considering this, there exists a need for improved devices and methods for the effective application of therapeutic hypothermia to structures in, on, or around the region of a human ear.

BRIEF SUMMARY OF THE INVENTION

Noise-induced hearing loss (NIHL) is an impairment resulting from irreversible damage to the hair cells or underlying neural structures in the cochlea as a result of noise exposure. The consequence of such damage is loss of hearing, that can occur acutely or over a period of time. The significant health problems presented by such hearing loss require development of new strategies to reduce or prevent it. We have shown that controlled and localized therapeutic hypothermia provided to the inner ear non-invasively and subcutaneously post-noise trauma conserves residual hearing. We have further shown that such a treatment may preserve sensitive neural structures against trauma. This is a novel technique that can be applied for preservation of hearing and balance during ototoxic insults, noise-exposure, traumatic brain injuries, exposures to blast, inner ear or middle ear surgeries, and chemotherapy. Cooling post-trauma can extend or postpone the critical time window of cell death by modulating multiple molecular and cellular pathways, which then allows for synergistic therapies. For example, one can envision local cooling after trauma to the ear (noise) "buying" the patient 24-48 hours. During this time, treatment can be combined with targeted drugs that are synergistic and provide a long-term benefit.

Certain embodiments structured according to the invention can be essentially described as an ice-pack for the ear. A system for treatment of a patient typically requires one thermal element or device per ear. Sometimes, a thermal device may be characterized as "passive". An exemplary passive device includes a compartment, or bladder, containing some sort of thermal "working fluid" or thermal mass. Sometimes, an embodiment may be made reference to as "active". An active device includes electronic elements to aid in cooling a localized area of a patient. Cooling devices may include both passive and active elements in workable combination. A cooling device may be structured for placement of the entire device, or only a portion thereof, into a cooling device such as a freezer to prepare a pre-chilled element for application of thermal therapy on a patient.

In one method of use, the device(s) is/are placed into a freezer until the working fluid/mass attains a temperature significantly lower than human body temperature. With the fluid/thermal mass at low temperature, the device is placed on the skull, in a region near, or around the ear. The therapy occurs as the device cools the skull (and the auditory structures within the skull) locally, over a time course dependent on the liquid volume, or thermal mass contained within the device.

An exemplary embodiment structured according to certain principles of this invention includes a thermal therapy device structured to interface in installed registration with an ear of a human head, the device being structured to place a heat transfer contact element in contact with the head at a localized area, the localized area extending only partially around a circumference of the ear. A therapy device may be structured to maintain an open pathway from the local environment to the ear canal of the ear on which the device is installed. In some cases, the open pathway, from the local environment to the ear canal of the ear on which the device is installed, passes through the device. Desirably, the therapy device is structured to maintain the heat contact element at a posterior position with respect to the ear canal of the ear on which the device is installed. For example, an ear opening may be structured to cause radial compression against an exterior surface of the ear, the opening being structured to receive an ear in penetration there-through during installation of the device on the head. An exemplary such ear opening is generally ovaloid to generate a torque against a top and a bottom of an ear to resist twisting of the device about an axis perpendicular to the head. Typically, the ear opening extends around an entire circumference of an installed ear. In certain cases, the ear opening may include an ear cone affixed to the therapy device at a large diameter open end of the cone to dispose a free-standing conic element that extends to a smaller diameter opening disposed at the opposite end of the ear cone. An internal conic surface of the ear cone may be structured to stretch and accommodate in compression against an exterior surface of an installed ear.

Sometimes, the thermal therapy device is passive. Other times, the device may include an electrically active thermal element.

An exemplary heat transfer contact element is embodied in a floor of a contact cavity. Desirably, the floor is transversely flexible and conformable to accommodate and conform under compression against the skin in the vicinity of the ear. A therapy device may also include a bulk cavity disposed in thermal communication with the contact cavity. In certain cases, the bulk cavity is further disposed in fluid communication with the contact cavity. Desirably, the bulk cavity is sized to hold between two-times and about twenty five-times the volume of a heat transfer media that is held in the contact cavity. In certain embodiments, a boundary between the contact cavity and the bulk cavity is defined by a step-change in cross-section at the boundary, and heat transfer between the contact cavity and the bulk cavity occurs across a cross-section disposed at the step-change location. Typically, the bulk cavity is insulated to resist heat transfer into the bulk cavity from the local environment. The bulk cavity may also be insulated to resist heat transfer into the bulk cavity from the head and/or structured to avoid contact with the head, and/or to resist heat transfer into the bulk cavity from the ear.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 5:
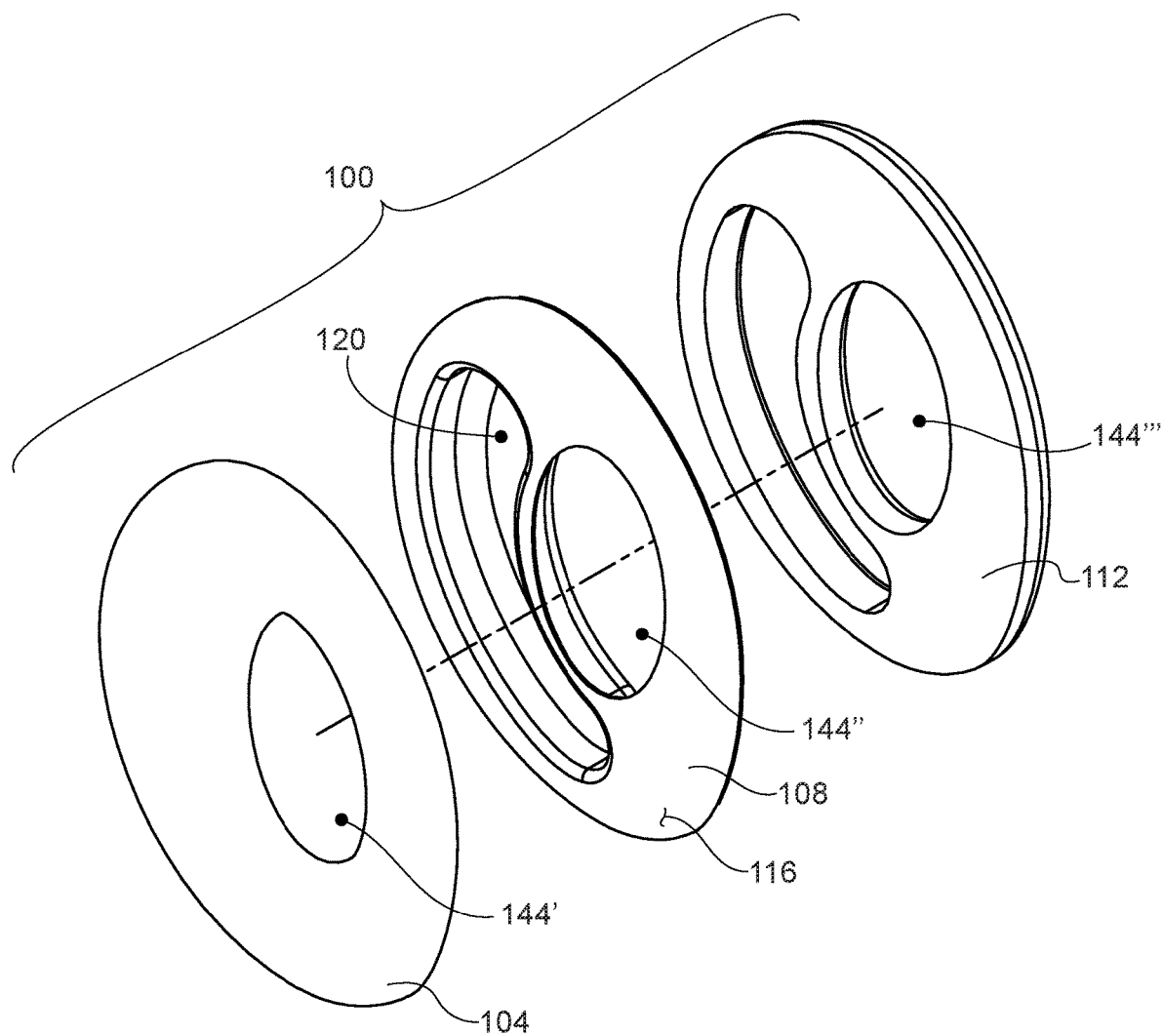
FIG. 5 is an exploded assembly view in perspective looking at the back side of the embodiment in FIG. 1.

An exemplary thermal device, or cooling pack assembly, is indicated generally at 100 in FIGS. 1 through 6. With particular reference to FIG. 5, embodiment 100 includes a rear cover 104, a membrane 108, and an insulator 112. Membrane 108 includes a substantially flat surface 116 that is formed to include or define a cavity 120. Cover 104 forms a rear surface of device 100.

Cavity 120 forms a contact heat transfer reservoir, and typically projects through insulator 104 to dispose its front or contact surface 124 proud of the exposed front surface 128 of insulator 112, such that surface 124 will contact the patient's skin near the ear. Desirably, cavity 120 provides a contact surface 124 that is structured to conform to the different anatomical surfaces of a variety of different patients. Also, it is desirable for membrane 108 to facilitate heat transfer from a patient into thermal/heat transfer fluid or media confined inside cavity 120.

Figure 6:
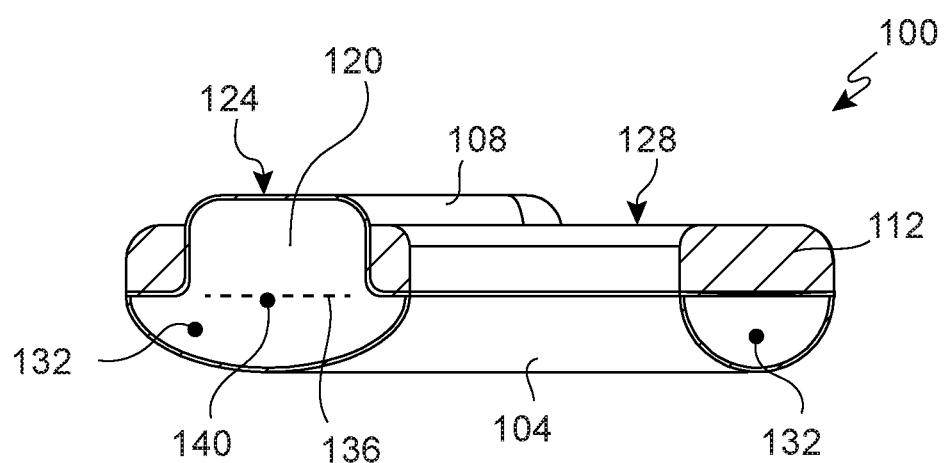
FIG. 6 is the cross-section view indicated in FIG. 2 by section lines 6-6 and looking in the direction of the arrows.

As illustrated in FIG. 6, cover 104 forms a cavity 132 in which to hold a bulk quantity of heat transfer fluid or media. Desirably, cover 104 includes an insulating property to resist heat transfer from a patient's ear, or the local environment, into cavity 132. Consequently, a cover 104 may include a plurality of layers of different materials (not illustrated). Cavity 120 and cavity 132 may be regarded as separated by an imaginary boundary 136 for purpose of structure definition. In fact, and in the case of illustrated embodiment 100, they may be in fluid communication and together form a combined reservoir cavity 140, in which is confined heat transfer media or fluid. It is preferred for a cavity 132 to be sized to hold a volume of heat transfer media that is about 2 times as great as a volume held in cavity 120. A workable cavity 132 may hold between 2 times and up to perhaps 25 times the volume that is held in a cavity 120, or even more.

Figure 1:
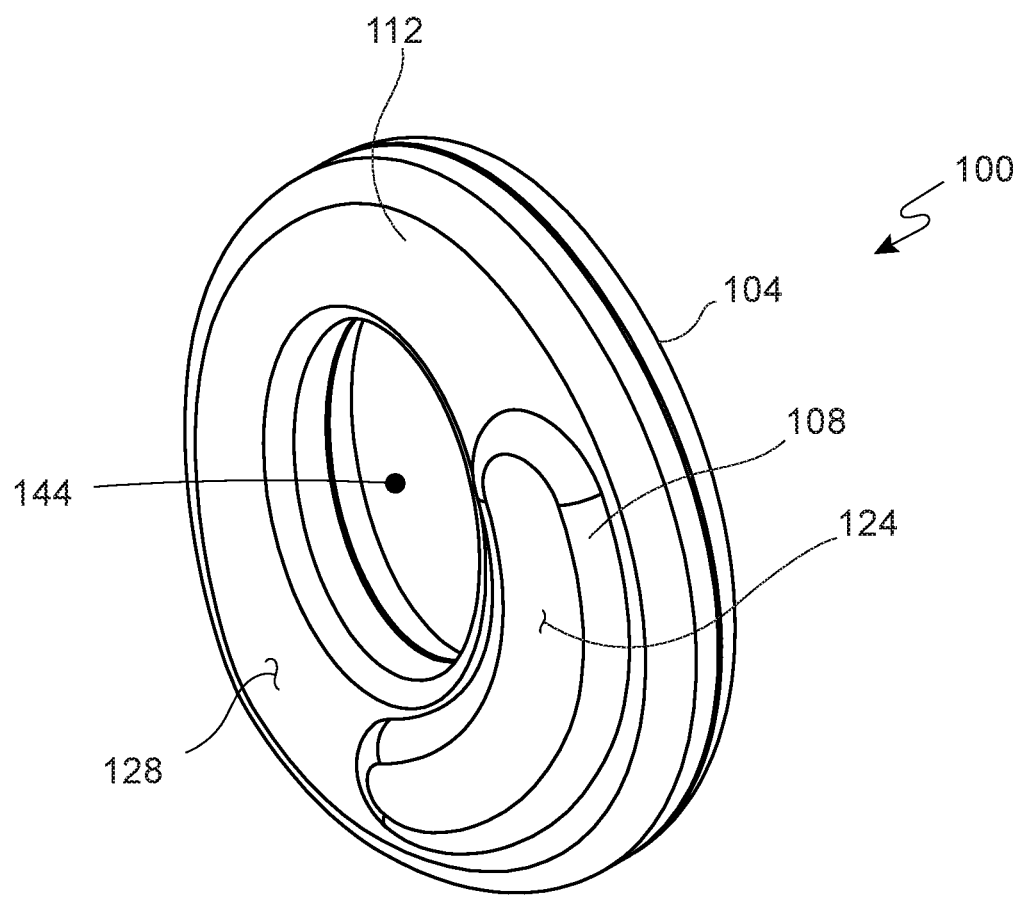
FIG. 1 is a perspective view looking at the front side, or alternatively the head-side, or contact portion, of a localized cooling pack assembly structured according to certain principles of the invention.
Figure 2:
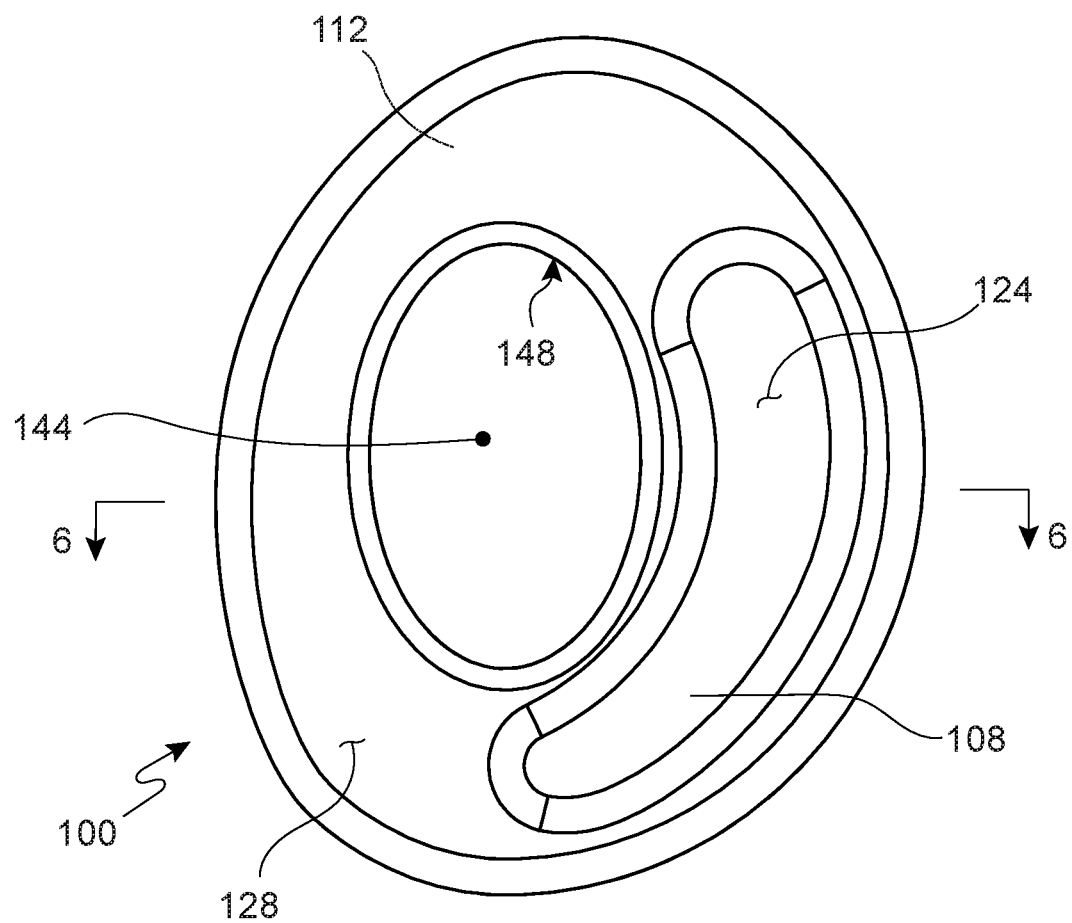
FIG. 2 is a front plan view of the device in FIG. 1
Figure 3:
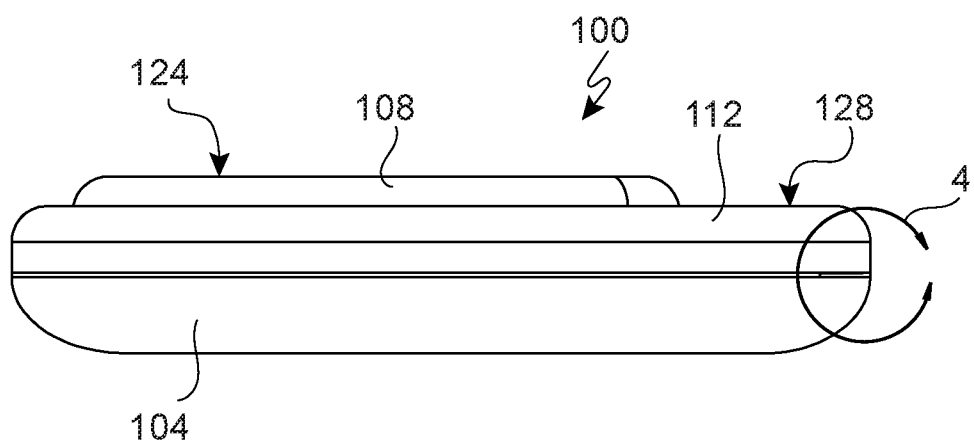
FIG. 3 is a side view in elevation of the device in FIG. 1.
Figure 4:
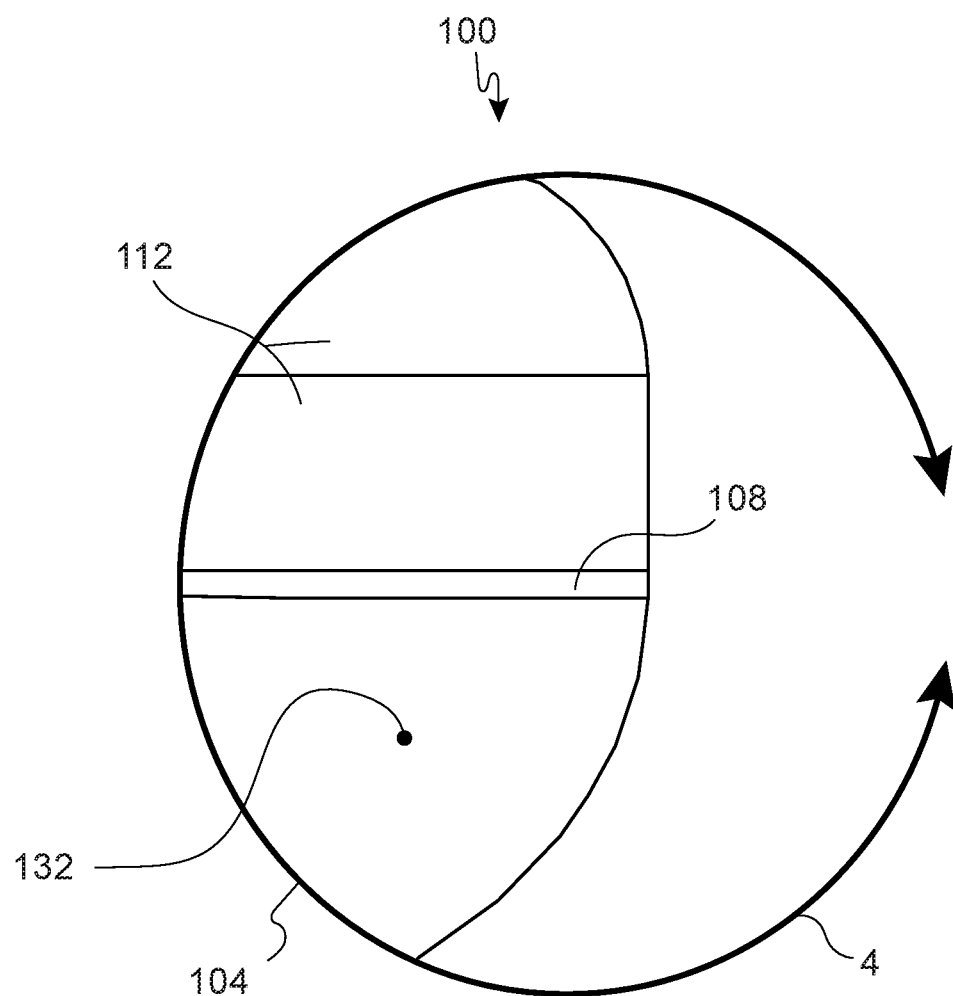
FIG. 4 is a close-up view of the detail indicated by circle 4 in FIG. 3.

A through-hole 144 is formed in device 100 to accommodate passage there-through of a human ear. Through-hole 144 is formed by corresponding through-holes 144', 144", and 144''' in cover 104, membrane 108, and insulator 112, respectively (see FIG. 5). As shown in FIG. 2, the perimeter 148 of through-hole 144 may be structured as a generally ovaloid cross-section, to fit in registration with the conventional shape of a human ear when the device 100 is installed on an ear. The non-circular cross-section of through-hole 144 resists twisting of the device out of desired registration to apply cooling to a particular location of the head.

Embodiment 100 is a passive cooling pack, and includes a cavity 140 that contains heat transfer media or fluid (liquid, gel, etc.). The entire device 100, or a component such as cavity 120, is typically chilled in a freezer, then applied as desired to a patient's head in the vicinity of an ear. Heat is removed from a localized portion of the patient's head, and absorbed by contact heat transfer reservoir 120. Heat gained in reservoir 120 is then transferred into bulk reservoir 132.

Figure 7:
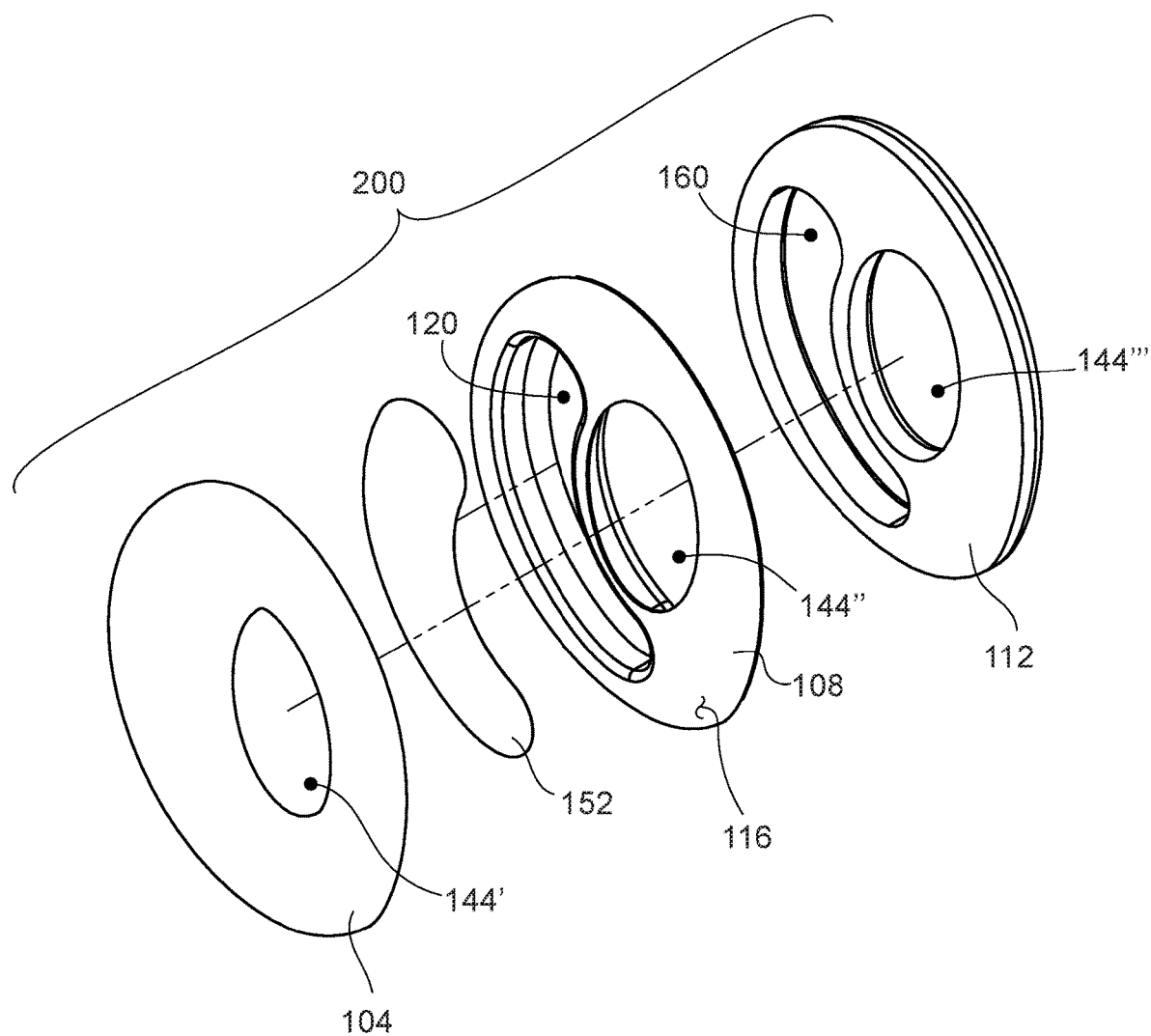
FIG. 7 is an exploded assembly view, similar to that in FIG. 5, of an alternative embodiment.
Figure 8:
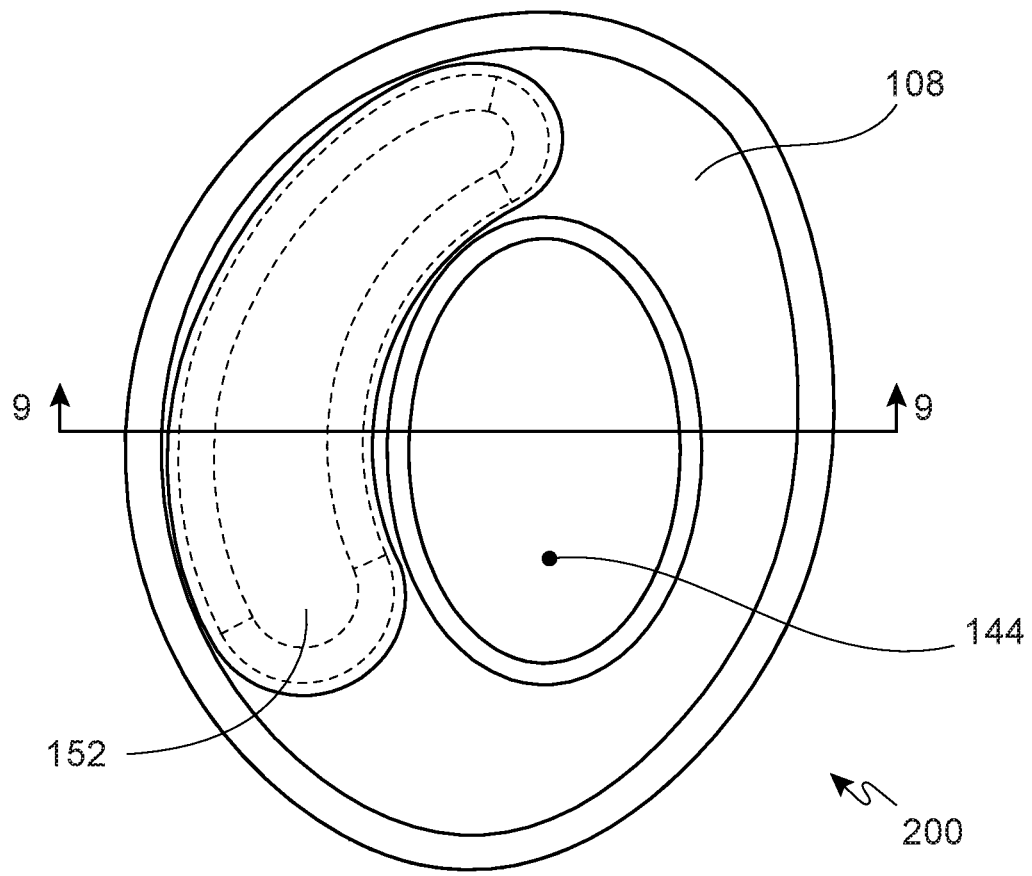
FIG. 8 is a rear plan view of the device in FIG. 7, partially assembled.
Figure 9:
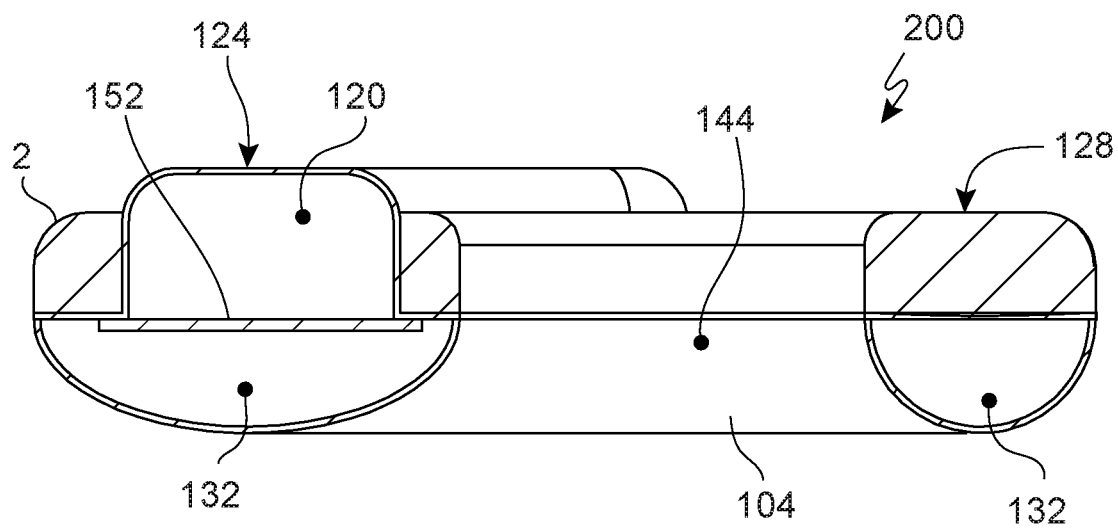
FIG. 9 is the cross-section view indicated in FIG. 8 by section lines 9-9 and looking in the direction of the arrows.

A two-reservoir embodiment is indicated generally at 200 in FIGS. 7-9. Embodiments similar to 100 and 200 may include certain elements in common, which are generally numbered accordingly. Superficially, embodiment 200 may appear to be identical to embodiment 100 in e.g., FIG. 1. However, embodiment 200 includes an internally-disposed physical barrier element 152 to define a fluid-tight separation between contact cavity 120 and bulk cavity 132. FIG. 8 illustrates barrier 152 stacked in registration on top of membrane element 108 to form a cap for cavity 120. Desirably, barrier element 152 facilitates heat transfer between media confined in respective cavities 120 and 132. Embodiment 200 therefore provides an opportunity to include different heat transfer media in each cavity. That permits tailoring a heat transfer profile or behavior for embodiment 200 compared to that available with embodiment 100.

Figure 10:
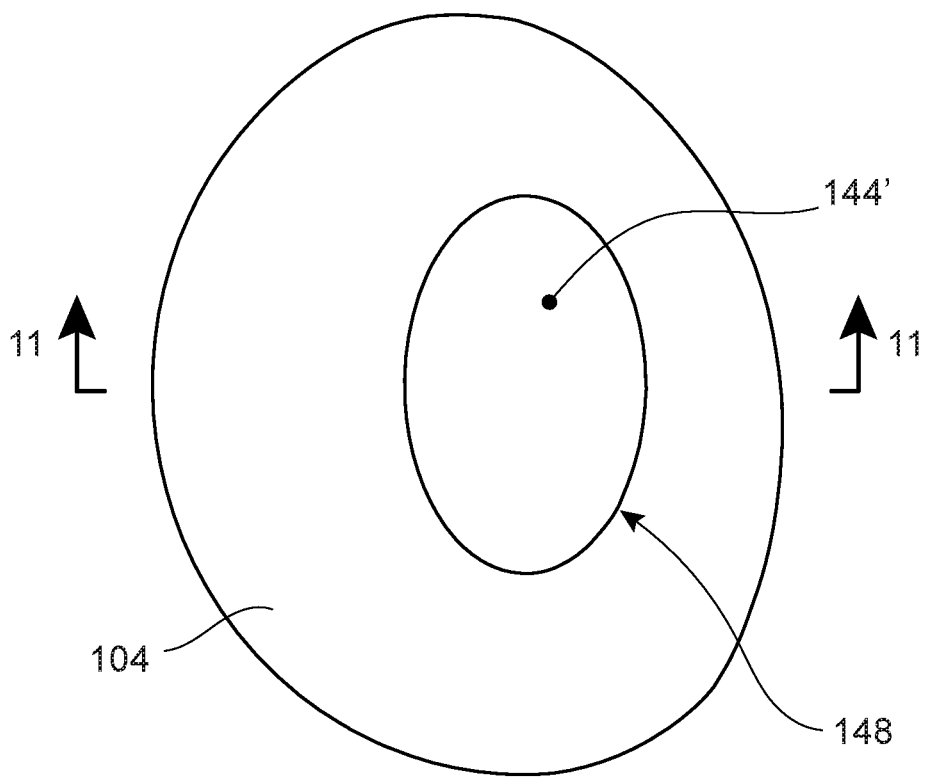
FIG. 10 is a rear plan view of a rear cover or bulk reservoir element.
Figure 11:
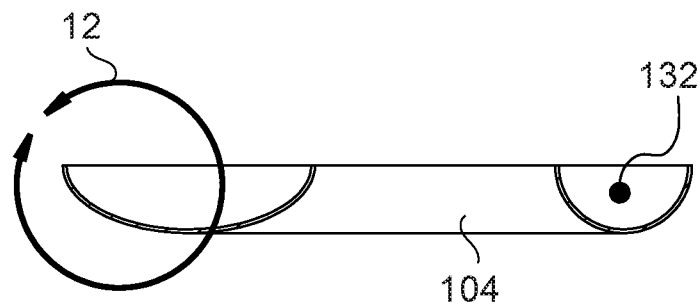
FIG. 11 is the cross-section view indicated in FIG. 10 by section lines 11-11 and looking in the direction of the arrows.
Figure 12:
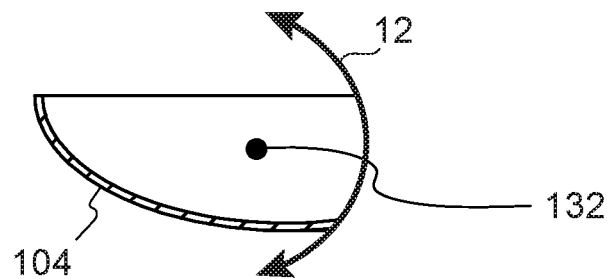
FIG. 12 is a close-up view of the detail indicated by circle 12 in FIG. 11.
Figure 13:
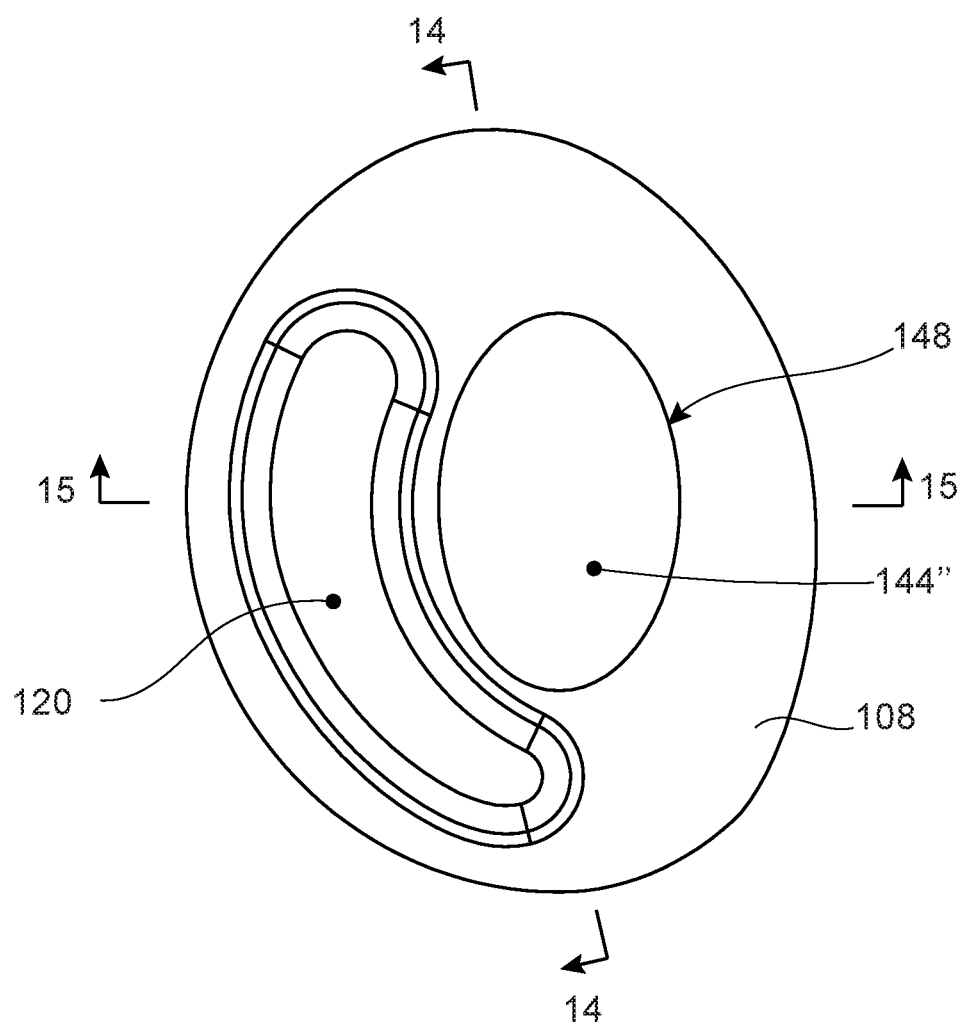
FIG. 13 is a plan view of a heat-sink reservoir element.
Figure 14:
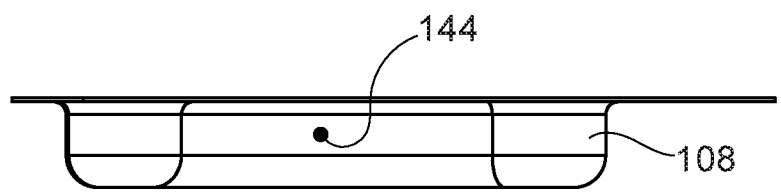
FIG. 14 is the cross-section view indicated in FIG. 13 by section lines 14-14 and looking in the direction of the arrows.
Figure 15:
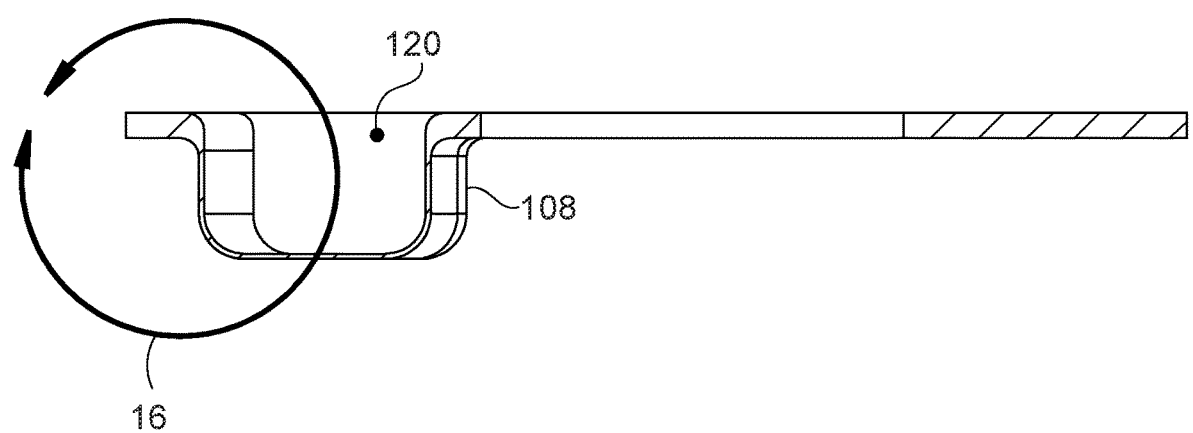
FIG. 15 is the cross-section view indicated in FIG. 13 by section lines 15-15 and looking in the direction of the arrows.
Figure 16:
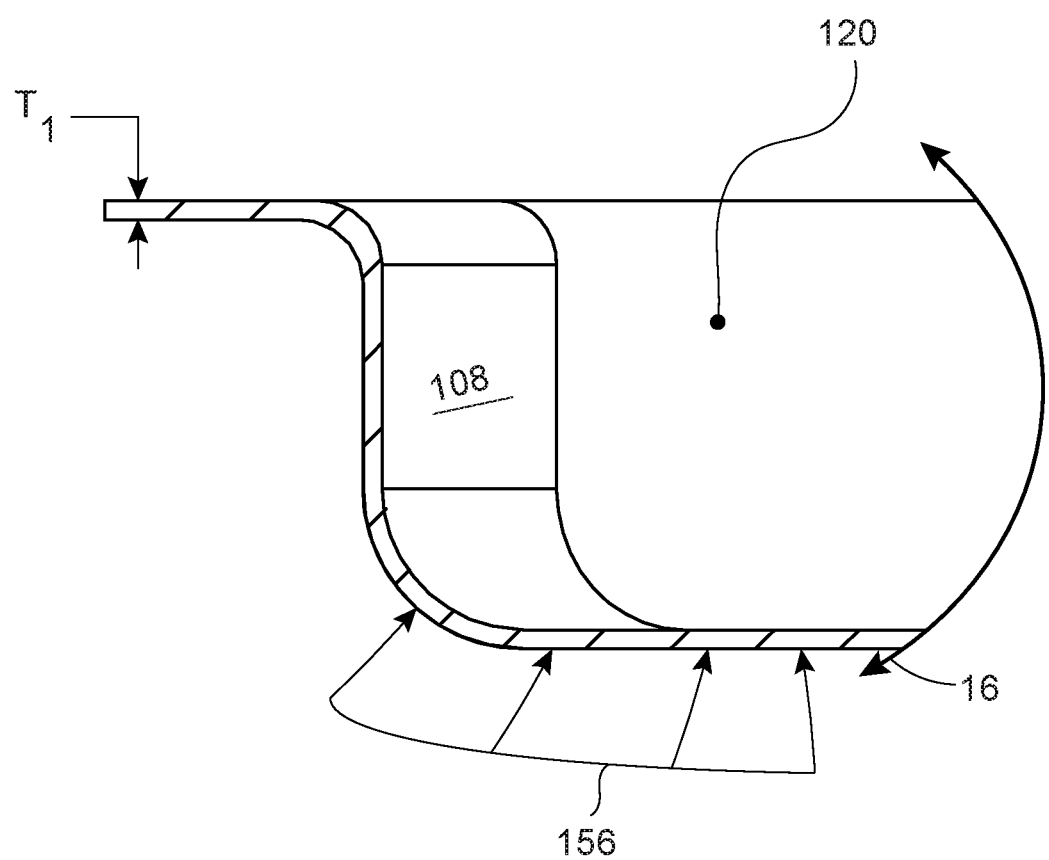
FIG. 16 is a close-up view of the detail indicated by circle 16 in FIG. 15.

Certain details of a workable rear cover 104 are illustrated in FIG. 10-12. A workable cover 104 may be formed from a flexible membrane, such as a polymer film, or from a rigid plastic, and the like. Certain covers 104 may expand like a balloon to accommodate loading or thermal expansion e.g., of heat transfer media. A workable rear cover 104 may sometimes be insulated to resist heat transfer from the environment into the confined heat transfer media. Certain rear covers may encompass a plurality of layers of different materials to provide a desired functionality.

Certain details of a workable membrane 108 are illustrated in FIGS. 13-16. A membrane may be fashioned by heat-forming, blow-molding, injection molding, or other known manufacturing method to generate a cavity defined by a membrane or thin wall. A currently preferred membrane 108 is made from polymer film having a thickness $T_1$ (see FIG. 16) of about 0.005-0.010" thickness. A preferred material includes a stretchable polymer film (e.g., polyethylene (LDPE, HDPE, LLDPE), polyester, nylon, Teflon, etc.). Such material may be used to manufacture either/both of cavities 120 and 132. The membrane/film desirably providing a deformable wall to contact and conform to a patient's head responsive to an applied pressure profile 156. The membrane forming patient-contact cavity 120 also preferably facilitating heat transfer there-through.

Figure 17:
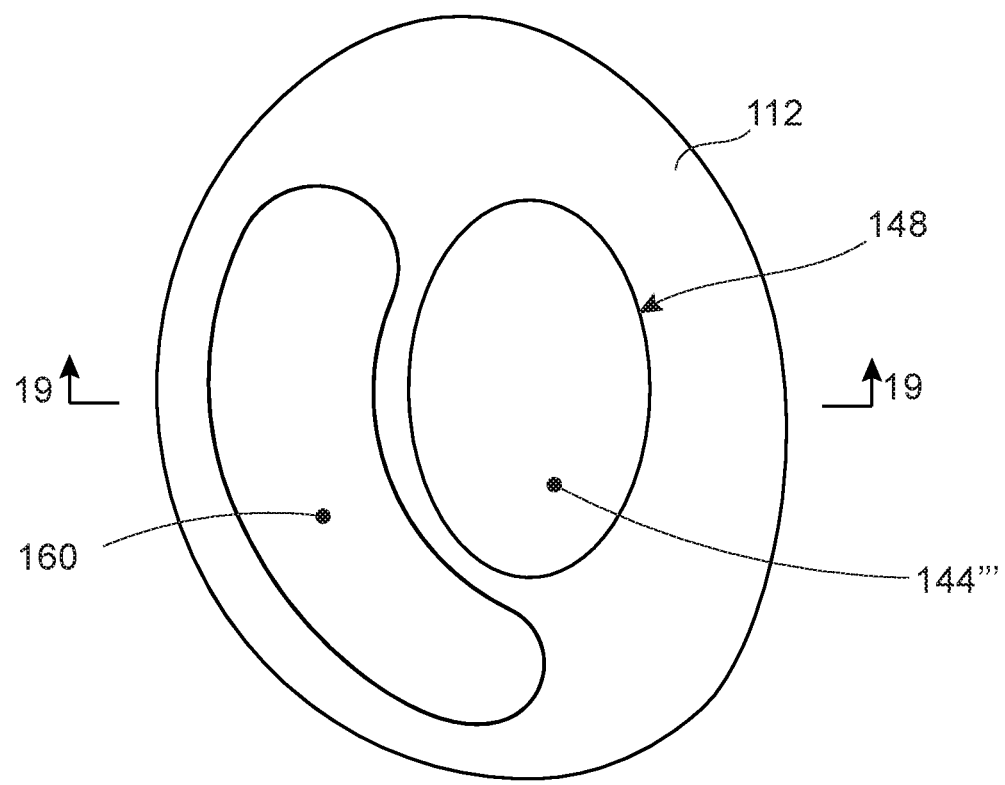
FIG. 17 is a plan view of an insulator element.
Figure 18:
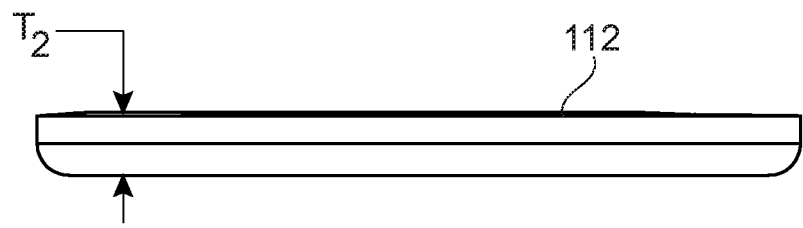
FIG. 18 is a side view of the insulator element in FIG. 17.
Figure 19:
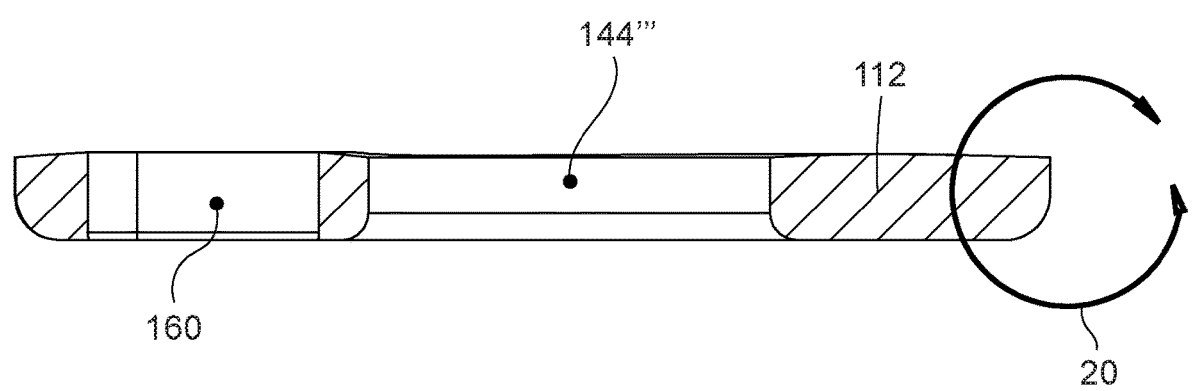
FIG. 19 is the cross-section view indicated in FIG. 17 by section lines 19-19 and looking in the direction of the arrows.
Figure 20:
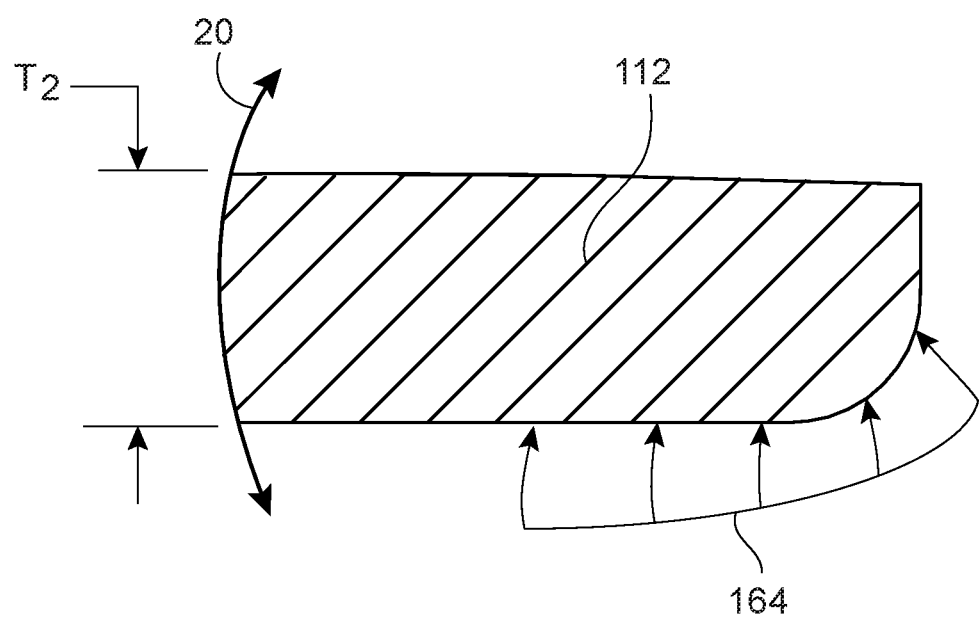
FIG. 20 is a close-up view of the detail indicated by circle 20 in FIG. 19.

Certain details of a workable insulator 112 are illustrated in FIGS. 17-18. A workable insulator resists heat transfer, and may be manufactured from open-cell foam, thermally-resistant material, skinned poly foam, or the like. Portions of insulator 112 also contact a patient's head, and are typically deformable or may be pre-shaped in a variety of different assemblies to comfortably accommodate between head shapes of different patients. The insulator 112 desirably providing a deformable surface to contact and conform to a patient's head responsive to an applied pressure profile 164. A currently preferred insulator 112 is made from foam having a thickness $T_2$ (see FIG. 20) of about 0.125-0.5" in thickness. A workable material to form an insulator 112 includes open/closed cell, thermally insulating polymer foam or rubber (closed cell/rubber, e.g., EPDM, neoprene, silicone, PVC, and polypropylene; open cell, e.g., polyurethane foam, open cell rubber).

The various elements may be fused together thermally, joined mechanically, or bonded with adhesives, and the like. Alternative manufacturing methods and suitable materials of construction will be apparent to one of ordinary skill in the art.

Figure 21:
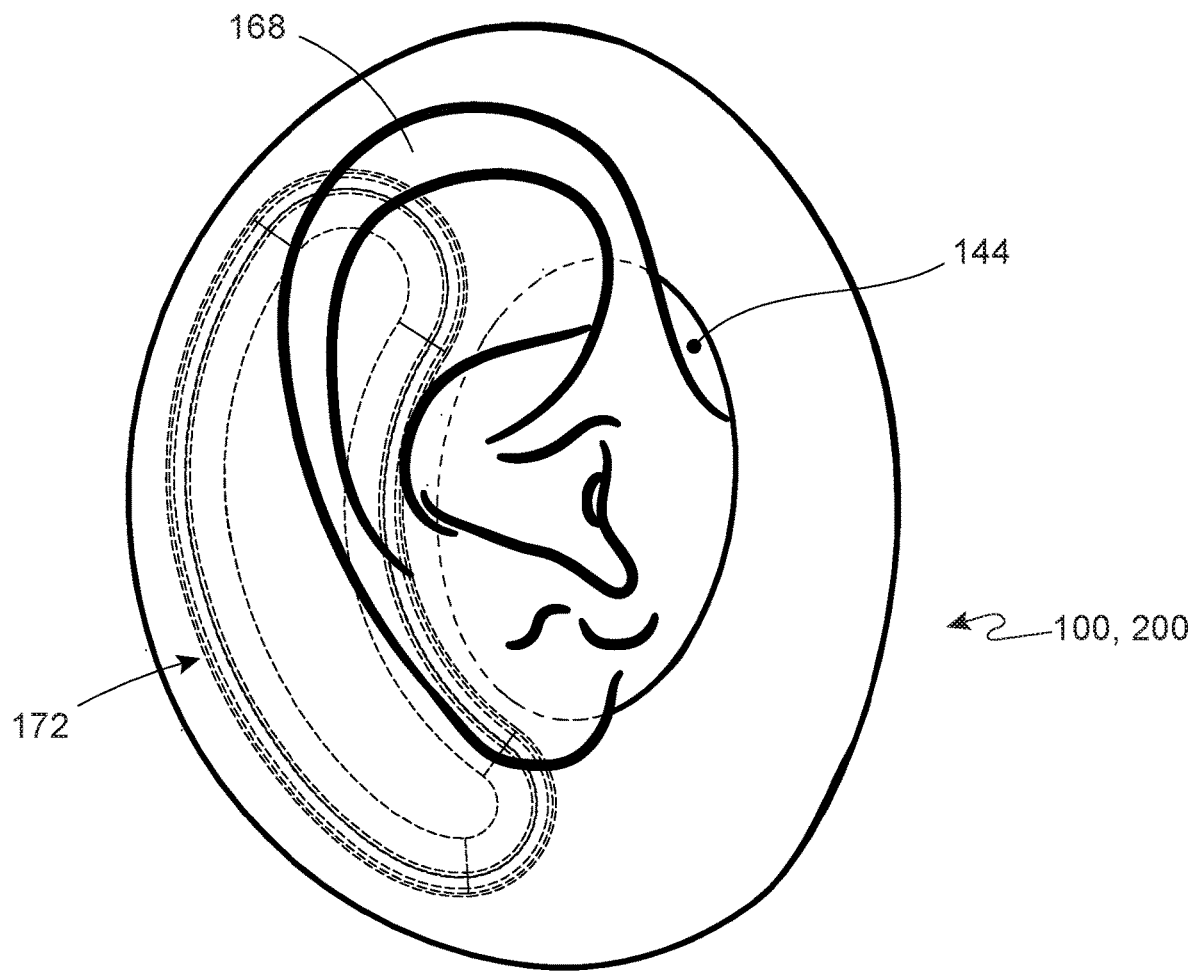
FIG. 21 illustrates a device according to certain principles of the invention installed with reference to an ear on a human head.
Figure 22:
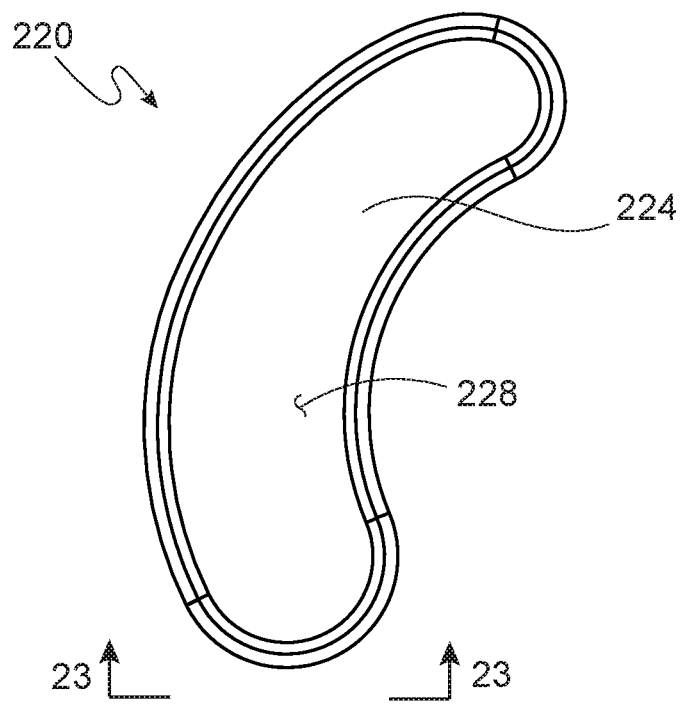
FIG. 22 is a plan view of another embodiment of a localized cooling pack assembly structured according to certain principles of the invention.
Figure 23:
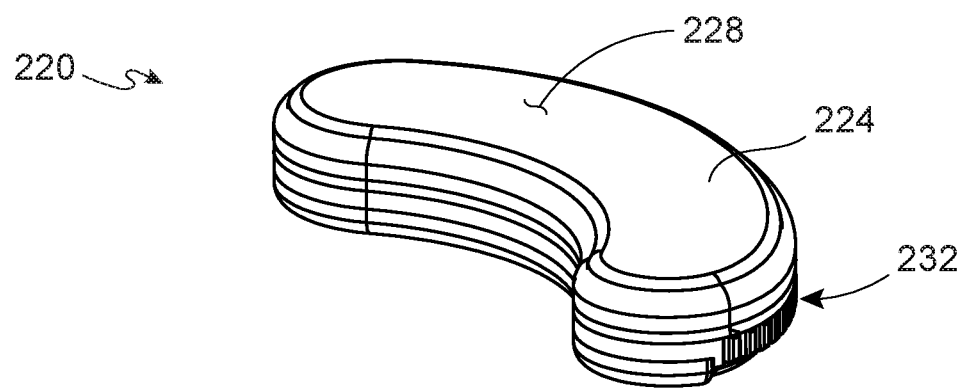
FIG. 23 is a perspective view of the embodiment in FIG. 22.

With reference now to FIG. 21, an embodiment such as 100 or 200 is illustrated in installed registration with respect to an ear 168 of a patient. The desired localized area of applied cooling (heat extraction or heat removal from the patient) is indicated by phantom-line structure indicated at 172.

Another embodiment is indicated generally at 220 and is described with reference to FIGS. 22-29. Embodiment 220 is an active device, and includes electronic components that provide heat transfer from a localized area of a patient's head. An active device such as 220 may sometimes include one or more passive component, which can be pre-cooled (e.g., frozen). Certain active devices 220 may extend thermal therapy for a time beyond the capability of a passive device, and may provide a desired programmable and time-variable cooling profile to a patient.

Figure 24:
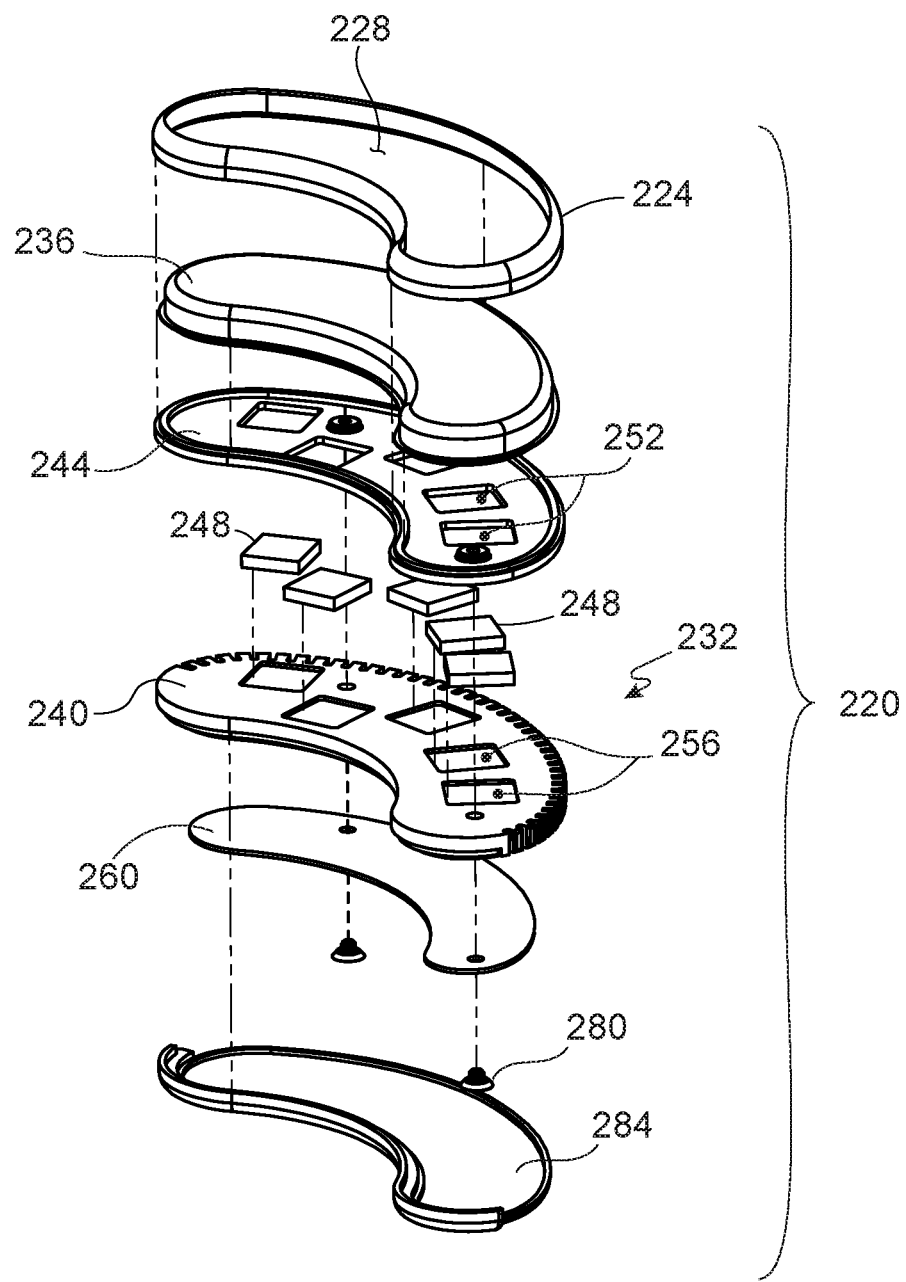
FIG. 24 is an exploded assembly view of the embodiment in FIG. 22.
Figure 25:
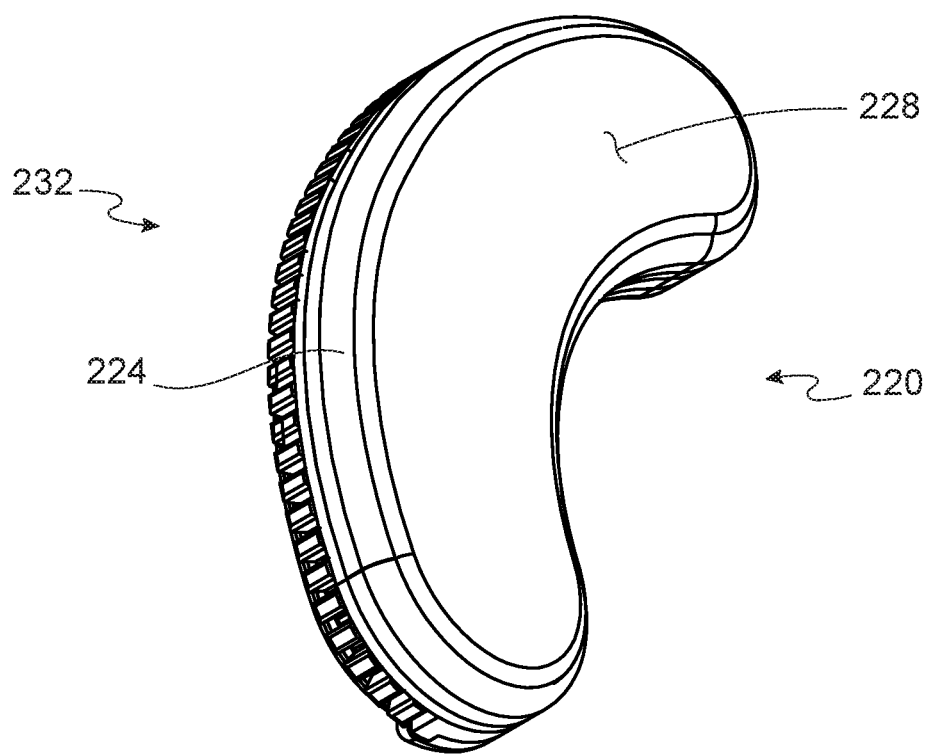
FIG. 25 is another perspective view of the embodiment in FIG. 22.
Figure 26:
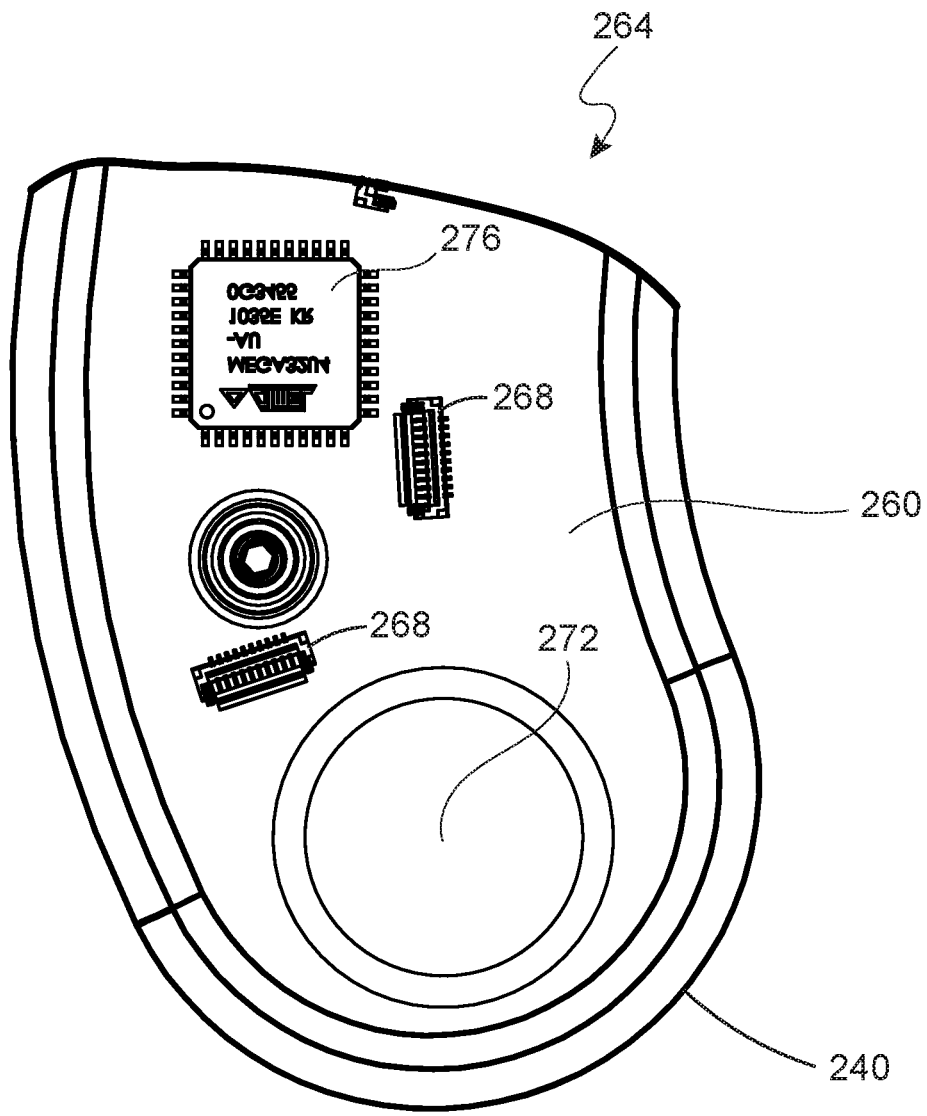
FIG. 26 is a close-up view of a portion of the embodiment in FIG. 22, partially disassembled.
Figure 27:
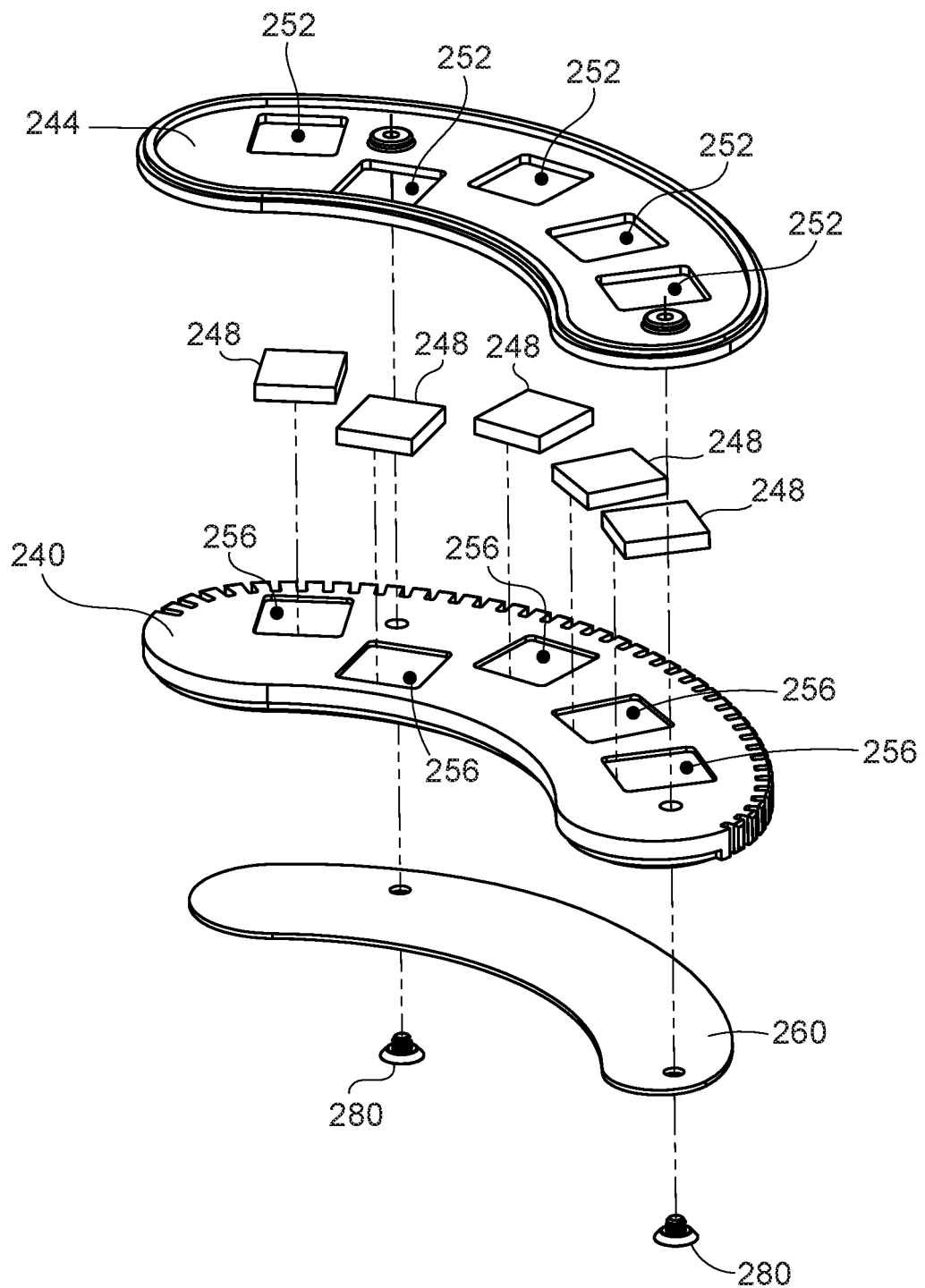
FIG. 27 is an exploded assembly view of a subassembly of the embodiment in FIG. 22.

Active device 220 includes a front cover 224 with a surface 228 structured and disposed for contact to the skin surface behind a patient's ear. A preferred cover 224 is flexible and accommodating to a patient's head shape. A heat-dissipating element, generally 232, is structured to dump heat from the device 220 to the local environment. An operable heat-dissipating element includes a series of fins and gaps provided in a thermally conductive heat sink material. With particular reference to FIGS. 24 and 27, a bladder 236 is installed in registration in contact with cover 224, and functions to draw heat from the patient's localized therapy area. A bladder 236 carries a heat transfer media, and may be pre-cooled (e.g., frozen like a passive ice pack). Bladder 236 is spaced apart from a heat sink element 240 by an insulating layer 244.

One or more (as illustrated, a plurality) thermoelectric heat transfer element 248 can be disposed to transport heat from the bladder 236 to the heat sink element 240. A workable heat sink element 240 may be manufactured from metal. A workable thermoelectric element 248 includes a Peltier device. A cooperating window 252 provides through-penetration of a device 248 and permits the cold side of an element 248 to contact and extract heat from the bladder 236. Sometimes, registration structure, such as a socket 256, may be provided as a manufacturing assembly aide to locate a thermoelectric device 248 with respect to the heat sink element 240.

The thermoelectric element(s) 248 are disposed in electrical communication with circuit board 260, which carries the electrical components (generally indicated at 264 in FIG. 26) for operation and control of the device 220. Electrical components that may be carried by circuit board 260 include: electrical connectors 268 to communicate with elements 248; on-board power supply, such as battery 272; and a micro-controller or integrated circuitry 276. The assembly or subassembly may be held together, at least in part, by one or more fastener 280.

A rear cover 284 provides a protective closure for the device 220. Desirably, rear cover 284 provides an insulation and spacing function to resist contact by the patient with heat sink element 240. In the illustrated embodiment, rear cover 284 is bonded around its perimeter to front cover 224.

Figure 28:
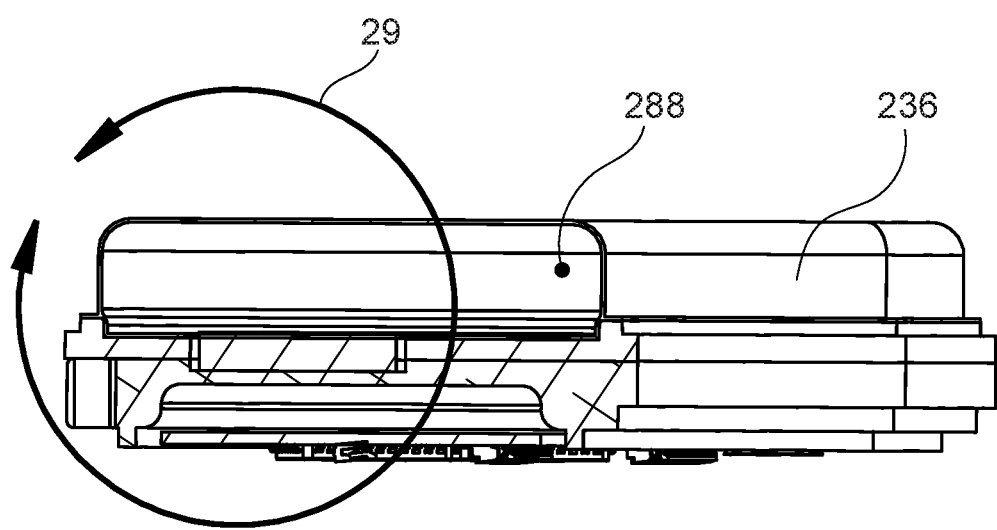
FIG. 28 is a cross-section view of the device in FIG. 23, with the top and bottom covers removed.
Figure 29:
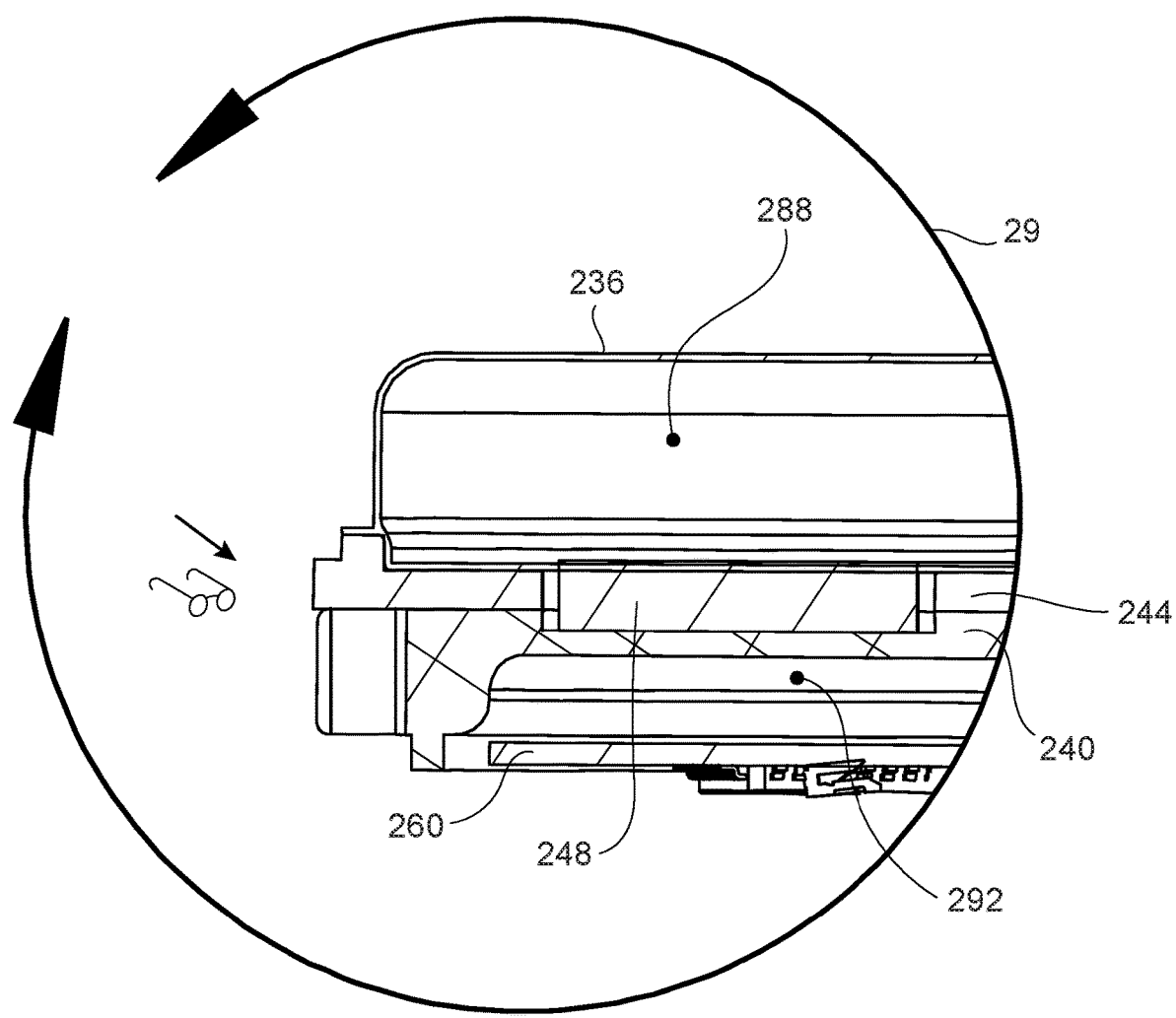
FIG. 29 is a close-up view of the detail indicated by circle 29 in FIG. 28.

With reference now to FIGS. 28 and 29, it can be seen how the various electronic and mechanical elements cooperate to cool heat transfer media confined inside the volume 288 defined by a bladder 236. An air gap 292 is provided to facilitate performance of the heat dissipation structure 232. Currently, air circulation through gap 292 is promoted by convection. Incorporation of a fan to drive air flow is within contemplation.

Figure 30:
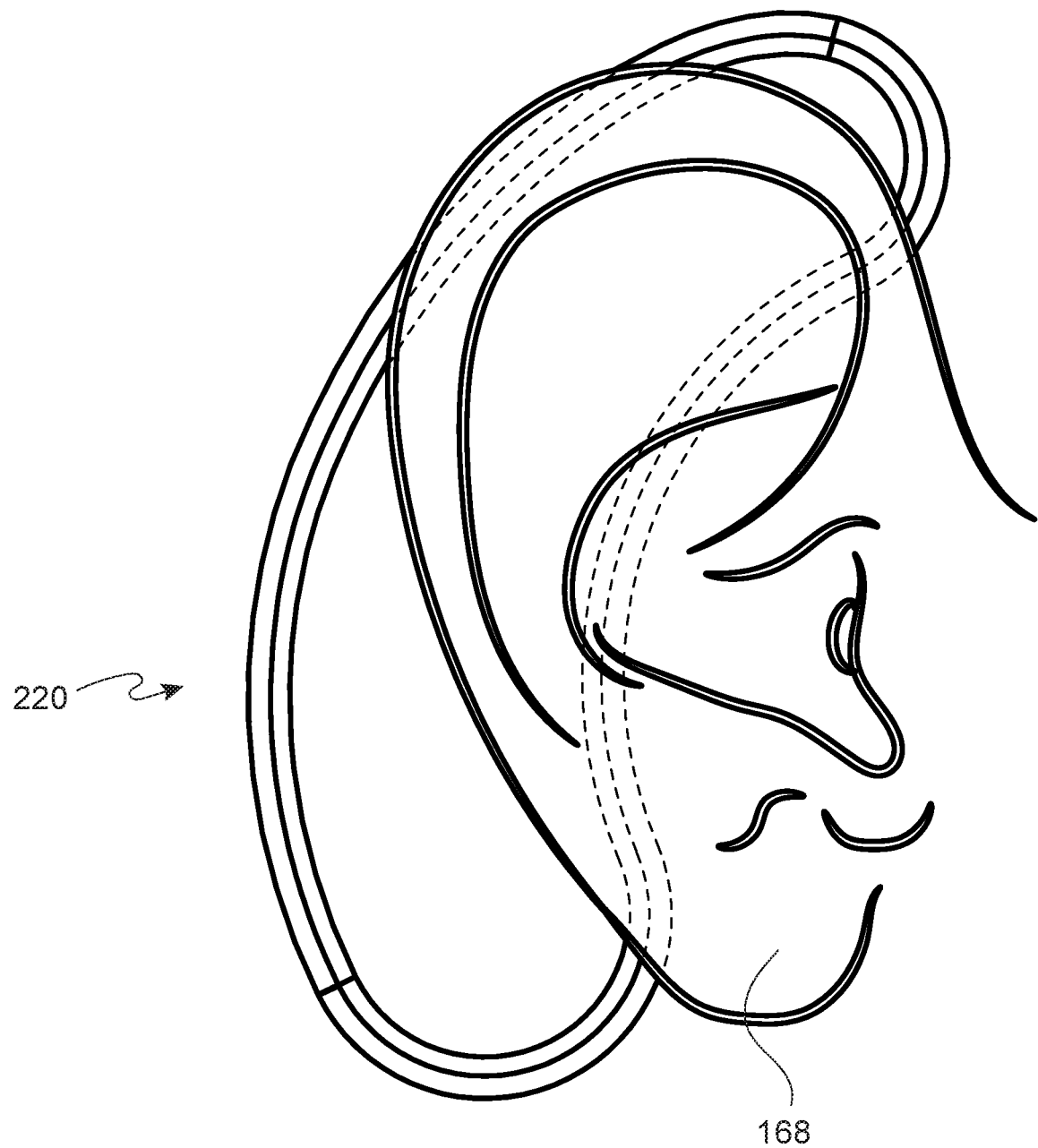
FIG. 30 illustrates another device according to certain principles of the invention installed with reference to an ear on a human head.
Figure 31:
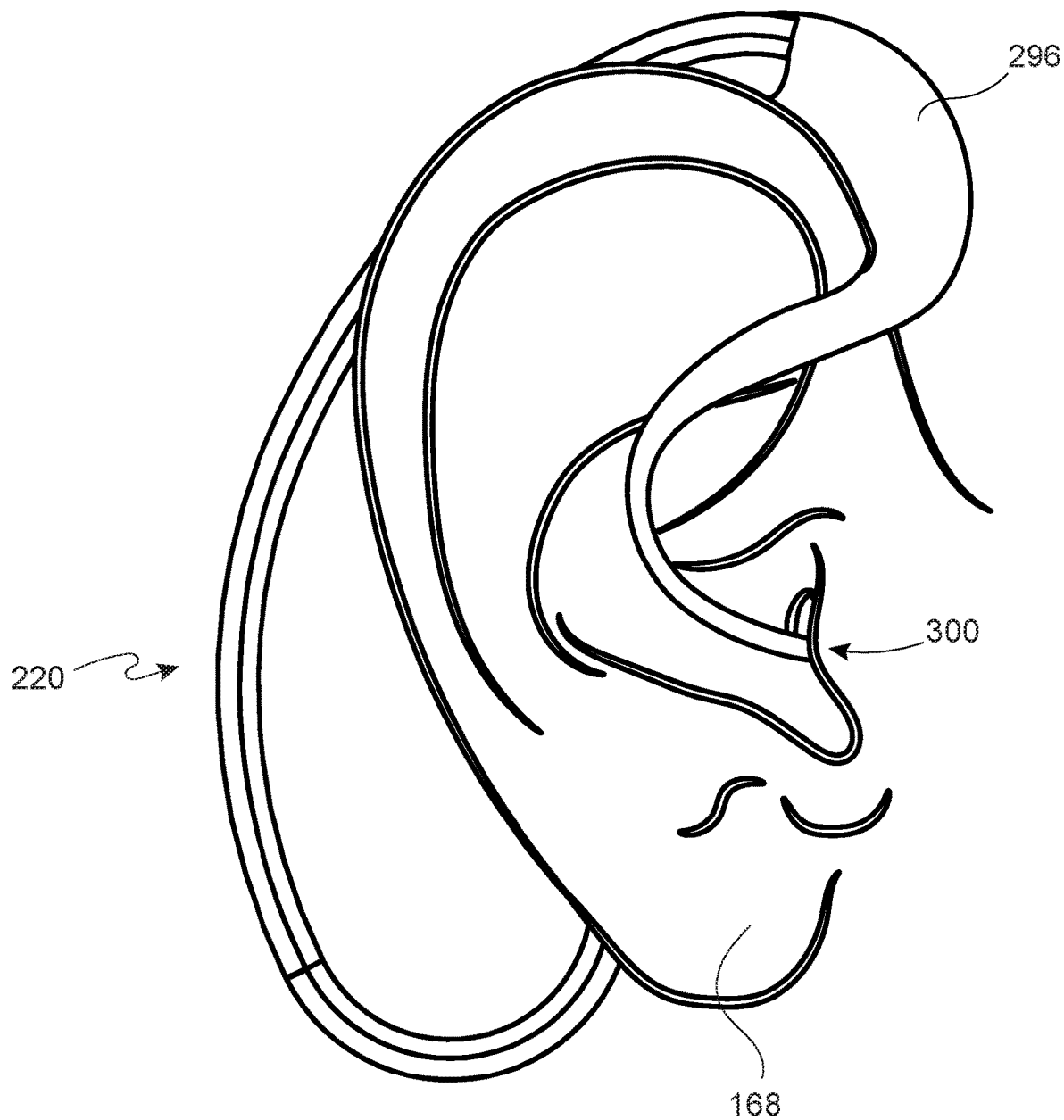
FIG. 31 illustrates another device according to certain principles of the invention installed with reference to an ear on a human head.
Figure 32:
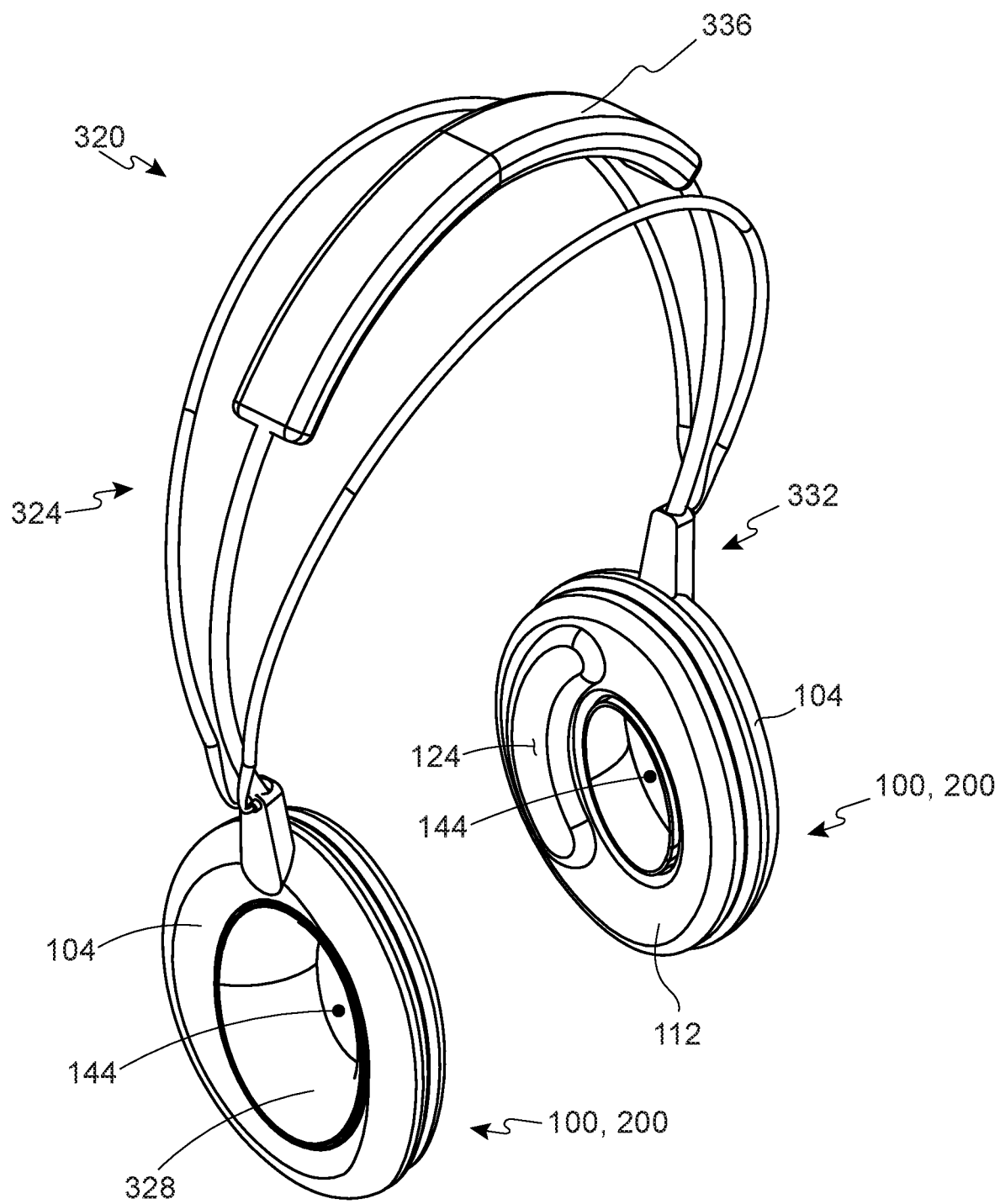
FIG. 32 is a perspective view illustrating an embodiment structured similar to conventional earphones.
Figure 33:
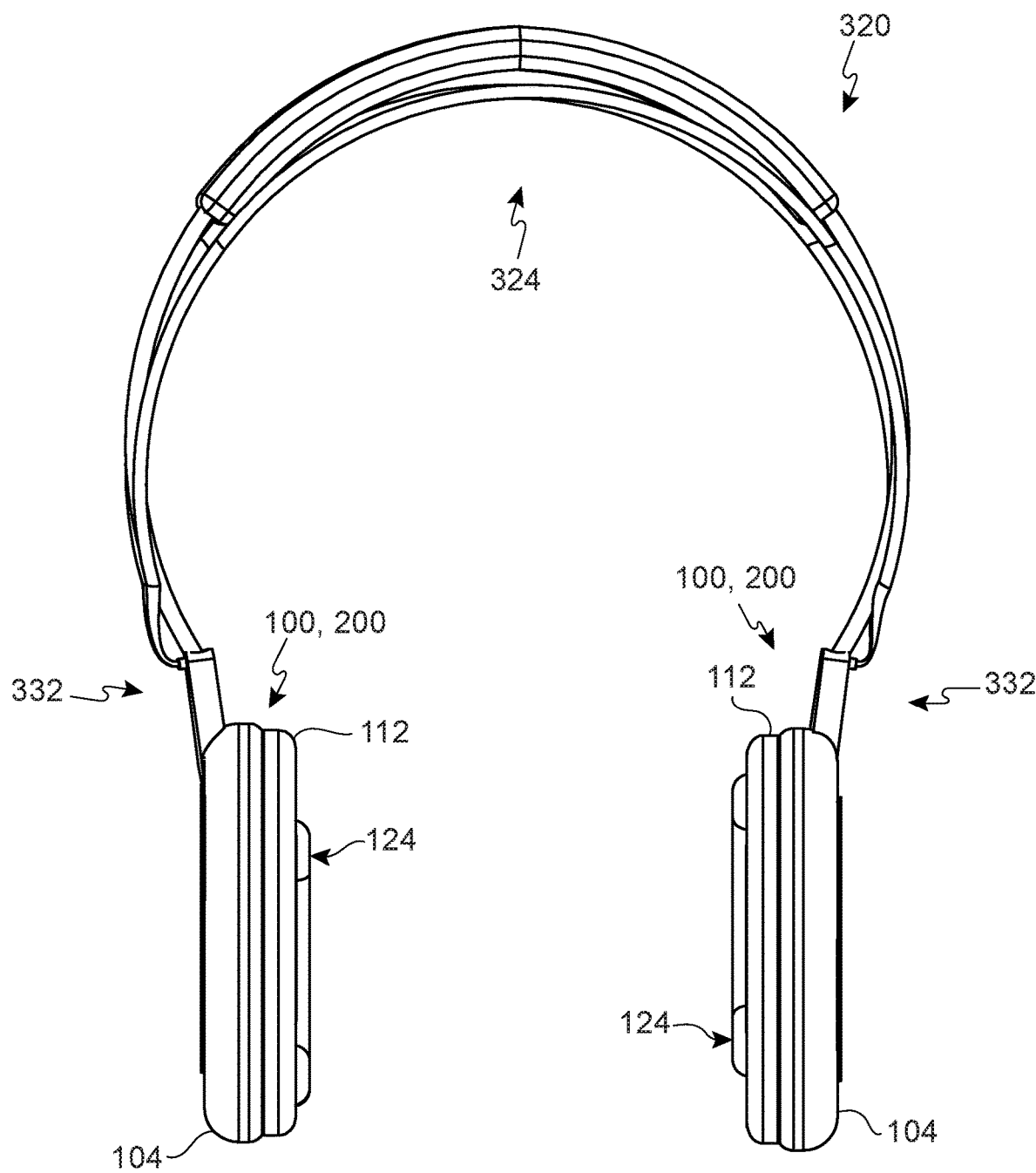
FIG. 33 is a rear view in elevation of the embodiment in FIG. 32.
Figure 34:
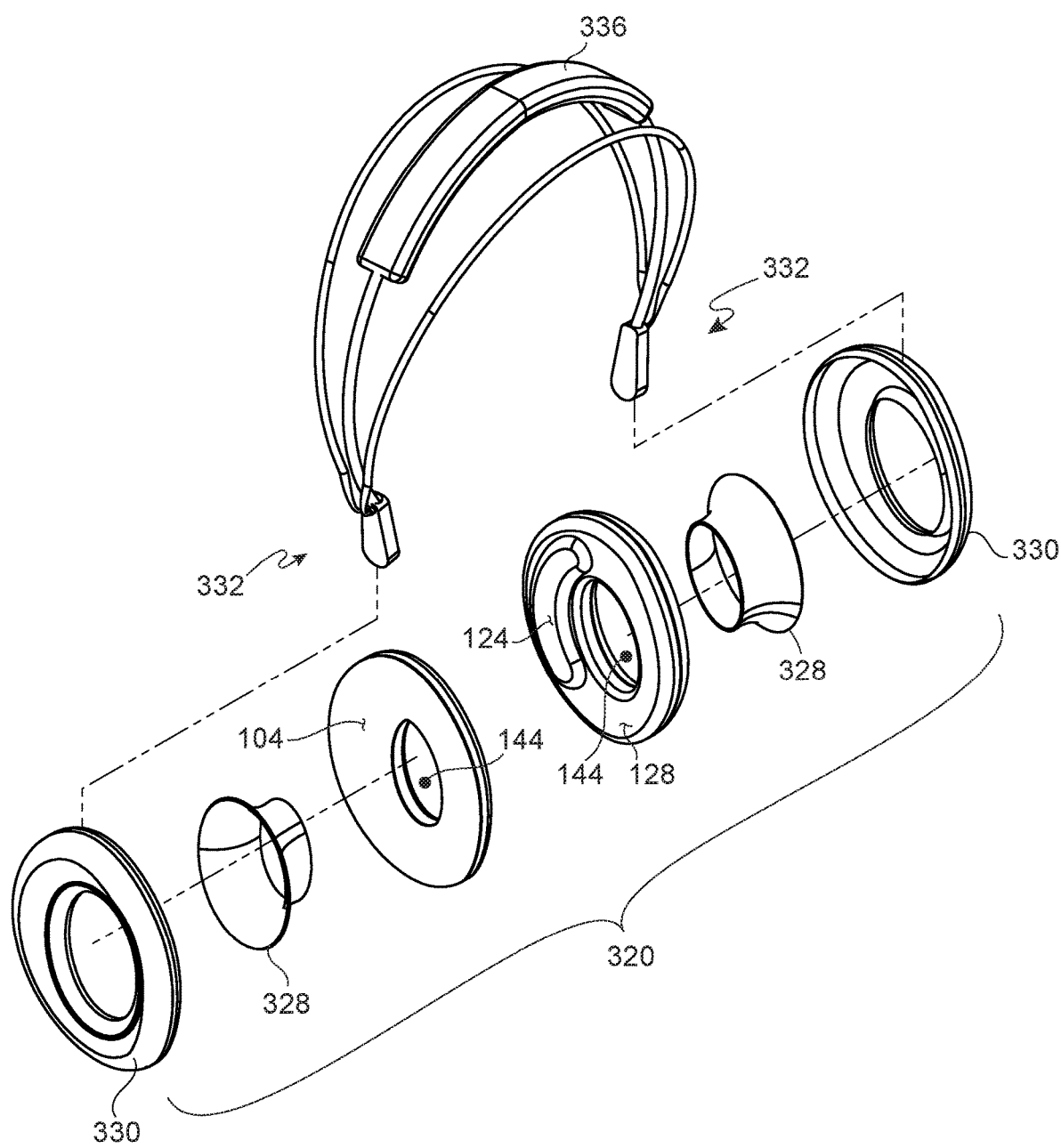
FIG. 34 is an exploded assembly view of the embodiment in FIG. 32.
Figure 35:
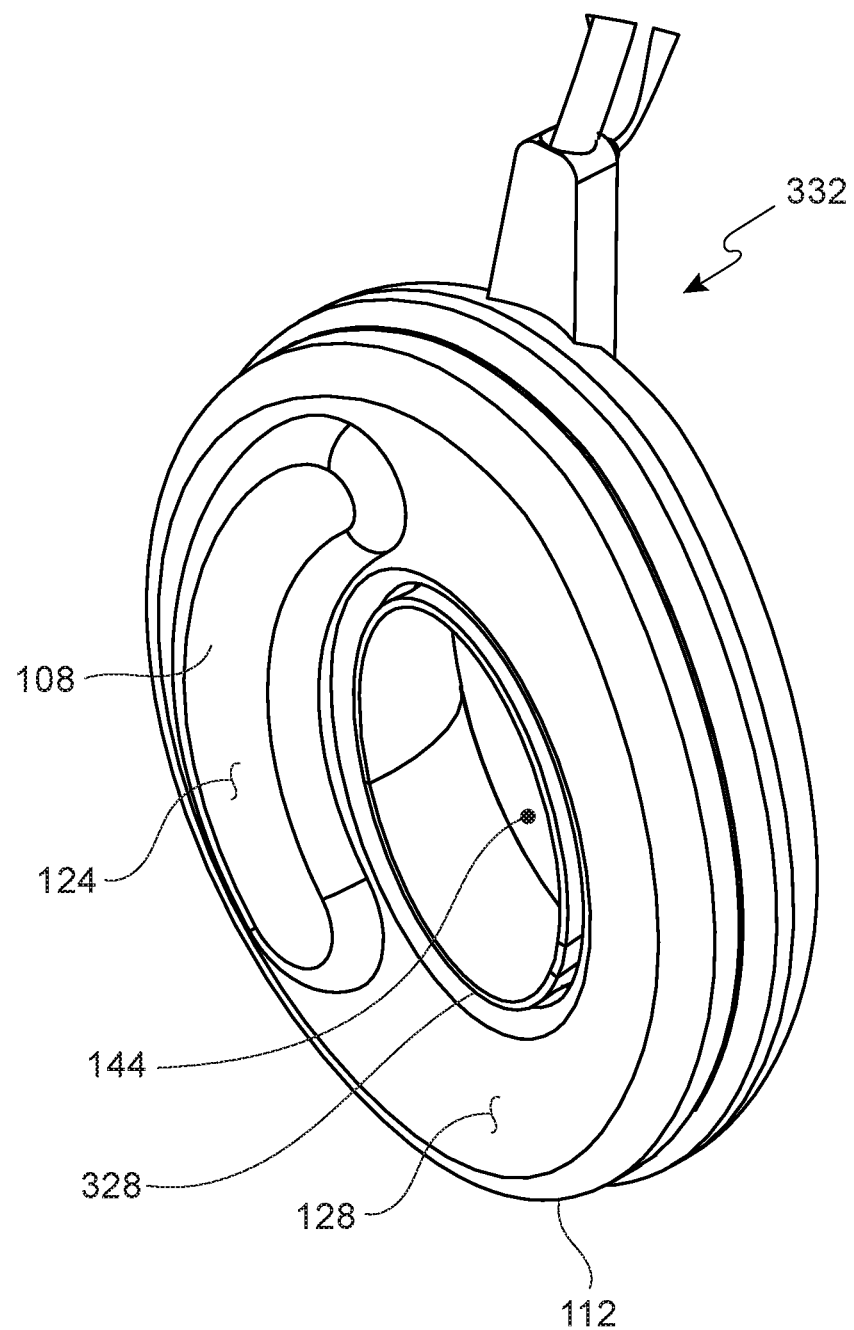
FIG. 35 is a perspective view at the inside, or head-contacting part, of a cooling pack illustrated in FIG. 32.

FIG. 30 illustrates an active embodiment 220 installed in registration with an ear 168 on a human head. An active embodiment 220 may alternatively be replaced by an entirely passive thermal therapy device having a cooperating size and configuration. An embodiment with an external configuration similar to that illustrated in FIG. 30 may be temporarily bonded onto the skin posterior to a patient's ear, or secured with tape or a wrap, or other workable retention structure. FIG. 31 illustrates optional mounting structure 296 affixed to a thermal therapy device and extending over the lateral side of the ear 168. In certain cases, and as illustrated, mounting device 296 may include a portion, generally 300, that extends into the ear canal for additional installation security.

The embodiment indicated generally at 320 in FIGS. 32-35 includes a pair of thermal therapy packs associated with a head band 324, similar to conventional stereo headphones. Although the illustrated thermal packs are externally structured according to embodiments 100 and 200, it is within contemplation that one or both may be replaced with an embodiment including an active heat transfer element.

Of note, embodiment 320 also illustrates optional ear cone elements 328. Cone elements 328 are structured from resilient elastic material that may stretch to facilitate installation of an ear there-through. Desirably, the cone elements 328 improve a grip on outer structure of an ear 168 by an installed thermal therapy device. It is currently desired for the ear cones 328 to be open at each end, to avoid interfering with the hearing of a patient that is undergoing thermal therapy. An operable ear cone 328 can be affixed to a thermal therapy device at a large diameter open end, leaving a free-standing conic section that extends to a smaller diameter opening disposed at the opposite end of the cone. As illustrated in e.g., FIG. 34, an ear cone 328 may be affixed to a shell element 330, and the shell element 330 may be associated with a thermal therapy device.

Connection structure, generally 322, may be included to facilitate coupling/decoupling a cooling pack to the headband 324. Connection structure 322 permits removal of a device for pre-cooling without exposing the entire assembly 320 to thermal change and potential temperature or condensate-induced damage. Desirably, a cooling device 100, 200, etc., is mounted with respect to the headband 324 to permit adjusting the device and band 324 to fit a device comfortably in registration on both sides of a patient's head. Typically, that includes degrees of freedom for rotation of each device about horizontal and vertical axes, and a length adjustment of band 324 between the devices. Also, headband 324 may include a compartment 336 in which to dispose electronics, power supply, wireless communication, control circuitry, and the like.

Figure 36:
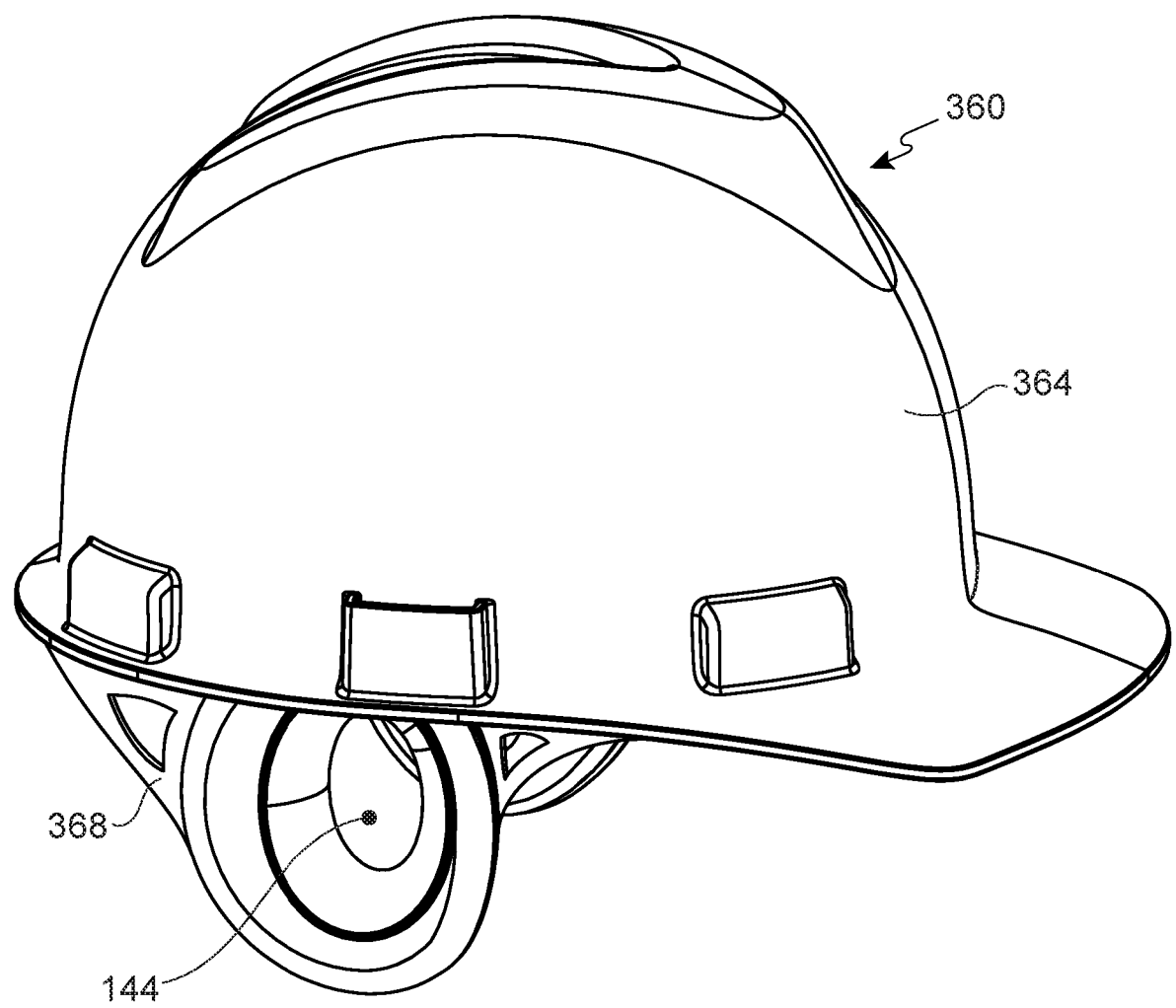
FIG. 36 is a perspective view, slightly from above, illustrating an embodiment adapted for association with a helmet or hat.
Figure 37:
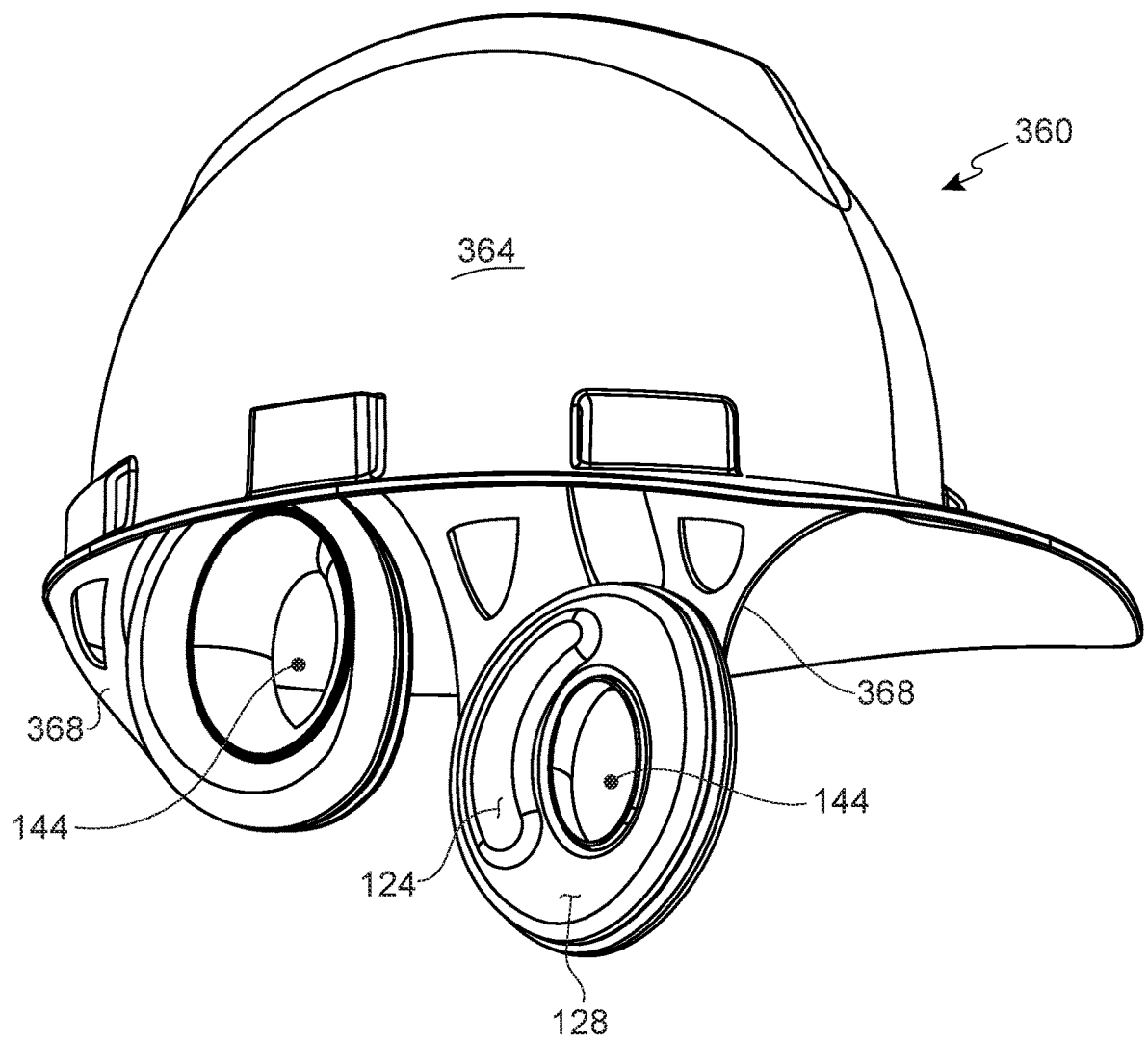
FIG. 37 is a perspective view, slightly from below, looking at the embodiment of FIG. 36.
Figure 38:
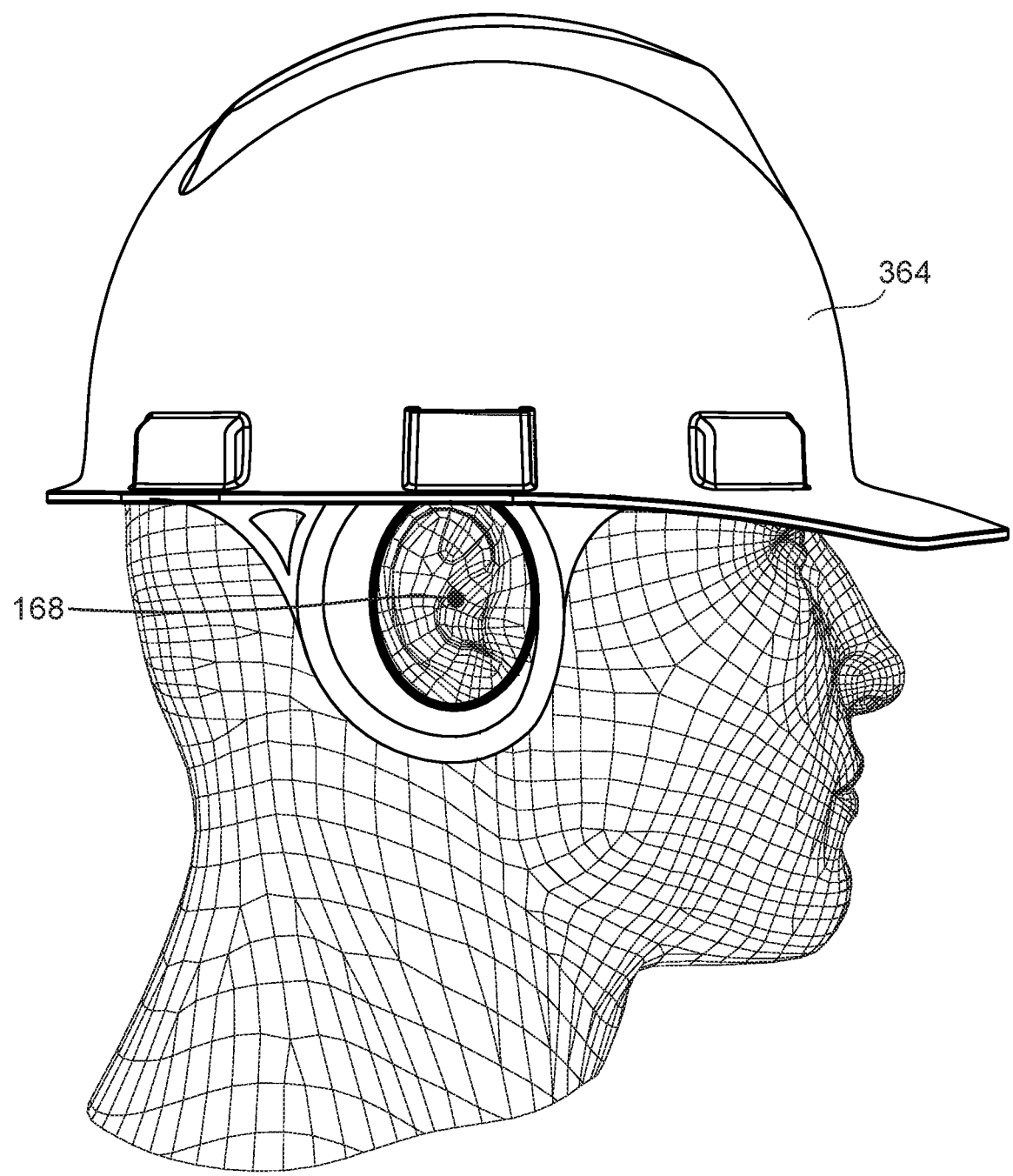
FIG. 38 illustrates the embodiment of FIG. 36 installed on a human head.

FIGS. 36-38 illustrate an alternative assembly, generally 360, including a helmet 364 structured to carry a pair of thermal therapy devices for installation on a human head. A cooling pack mounting band 368 may be adapted to removably hold a pack in position for desired therapy. Desirably, the pack is removable (and sometimes may even be partially dis-assembled) for safe cooling or freezing of one or more removed element.

Figure 39:
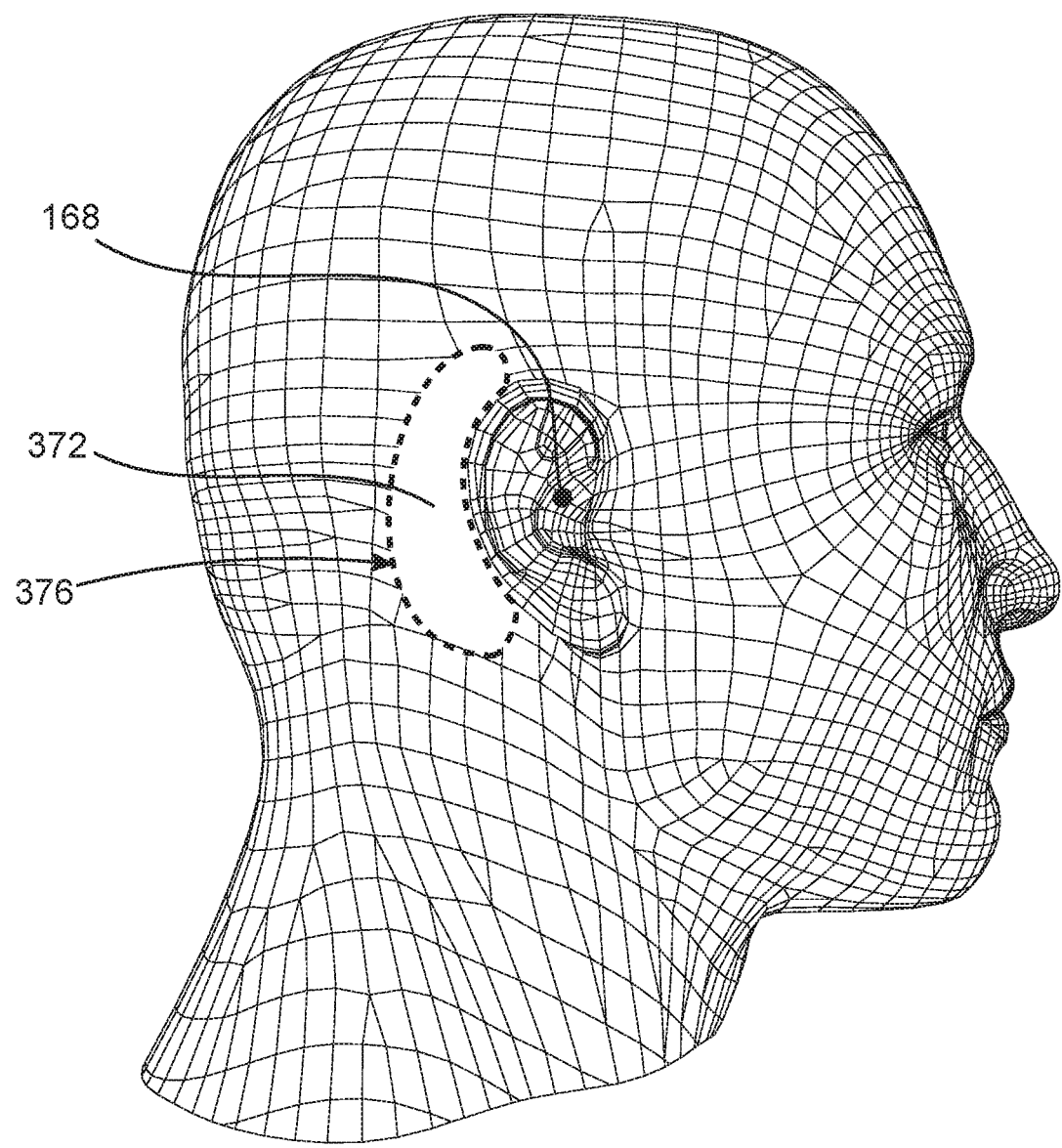
FIG. 39 is a perspective view of a human head indicating a preferred area for application of therapeutic cooling.

FIG. 39 illustrates a desired localized therapy area 372 that is bounded by a perimeter 376. Area 372 is roughly bean-shaped, and may be characterized as an arcuate shape having a center of curvature on the earhole side and extending partially around a circumference of an ear. Area 372 is desirably disposed to approximately abut a posterior ear surface, substantially as close as a thermal therapy device can comfortably fit. It is currently preferred to apply thermal therapy (cooling) only in the localized area 372. Consequently, a contact heat transfer element e.g., cavity 120, is shaped to fit within the perimeter 376. Workable contact shapes for heat transfer patient contact surface 124 include round, rectangular, and arcuate to generally match the bean shape defined by perimeter 376.

Figure 40:
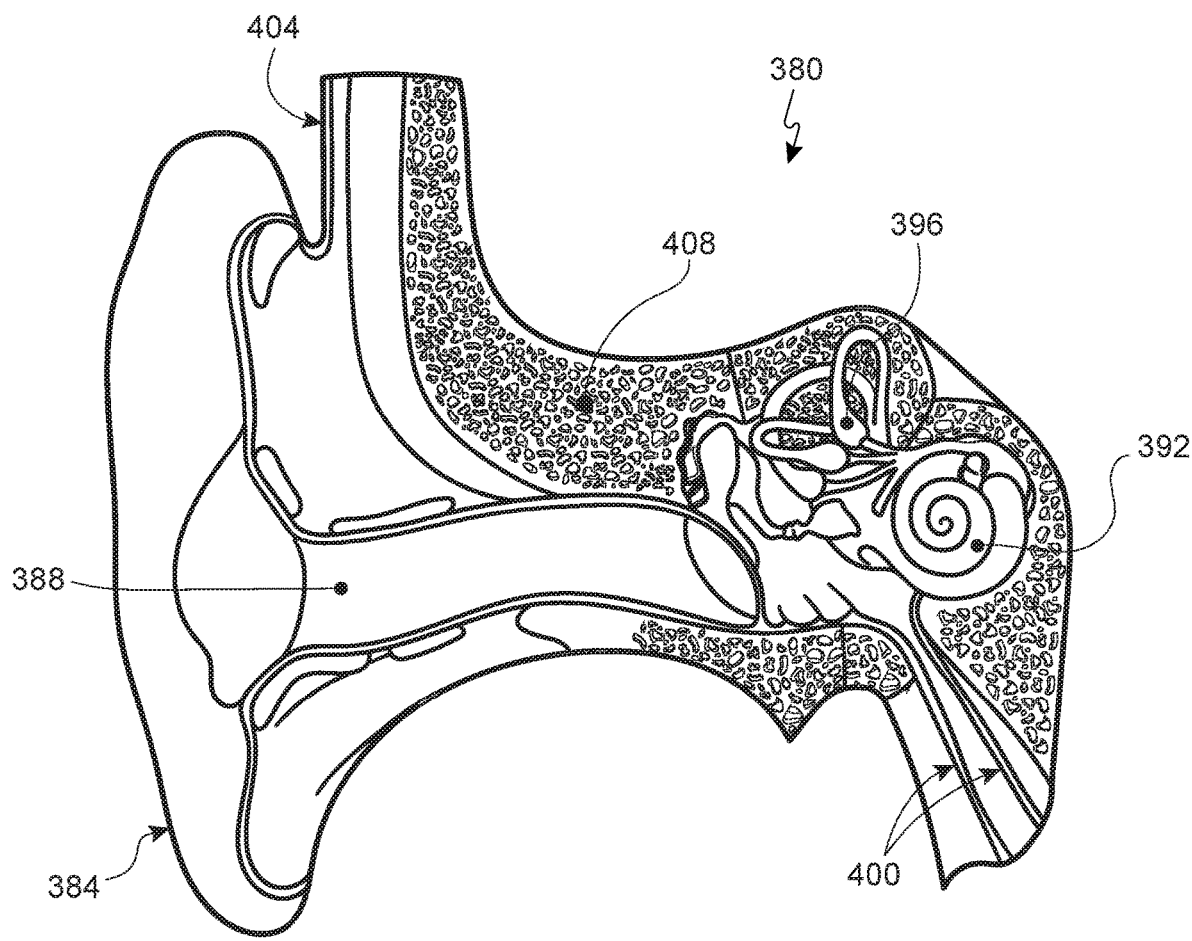
FIG. 40 is a cross-section through a human head illustrating the internal structures effected by cooling therapy.

FIG. 40 illustrates the internal auditory system structures of a human head, generally 380, that are desirably effected by thermal therapy. Inner ear structures 380 include: outer ear 384; ear canal 388; cochlea 392; semi-circular canals (vestibular system) 396; nerve structures (auditory and vestibular 400; skin over the skull 404; and bone of the skull 408. It is believed that currently preferred thermal therapy devices act primarily to transfer heat from the structures of the inner ear by way of conduction through bone 408.

Figure 42:
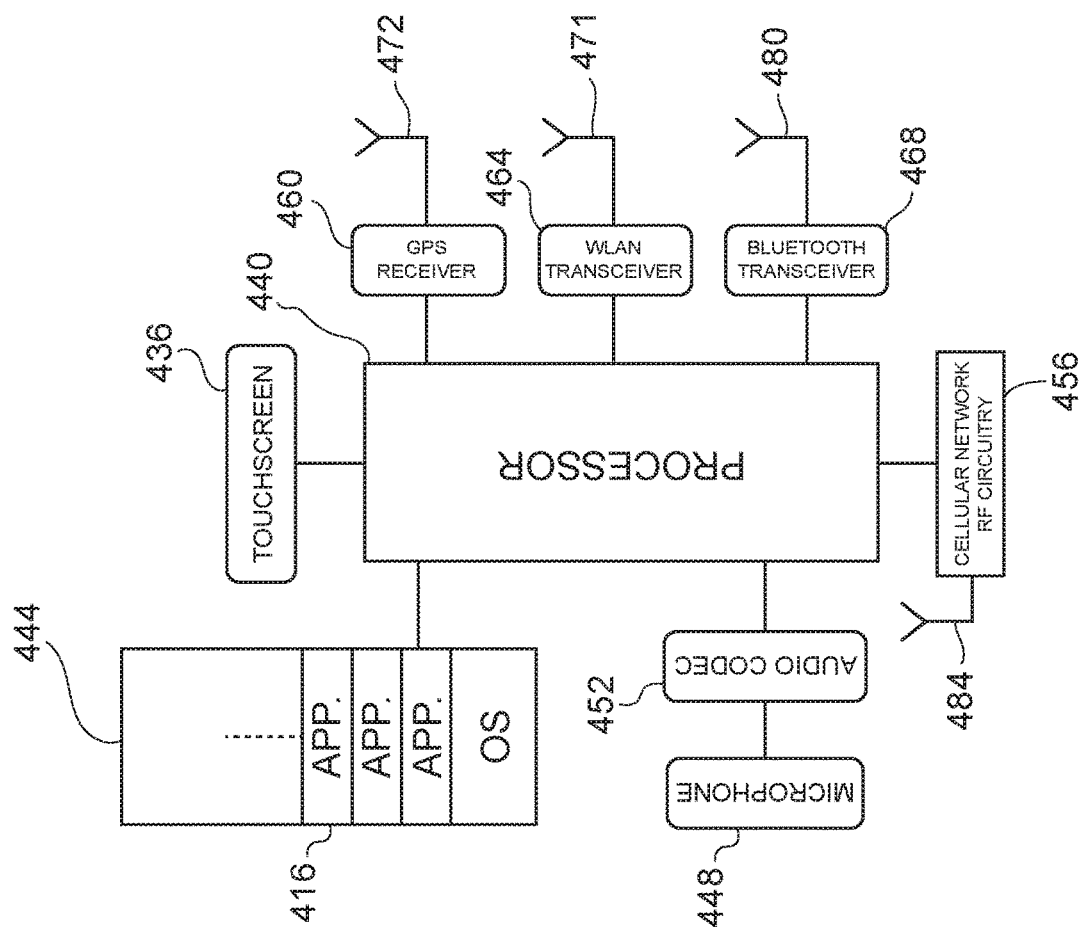
FIG. 42 illustrates an exemplary and workable hardware/software architecture.
Figure 41:
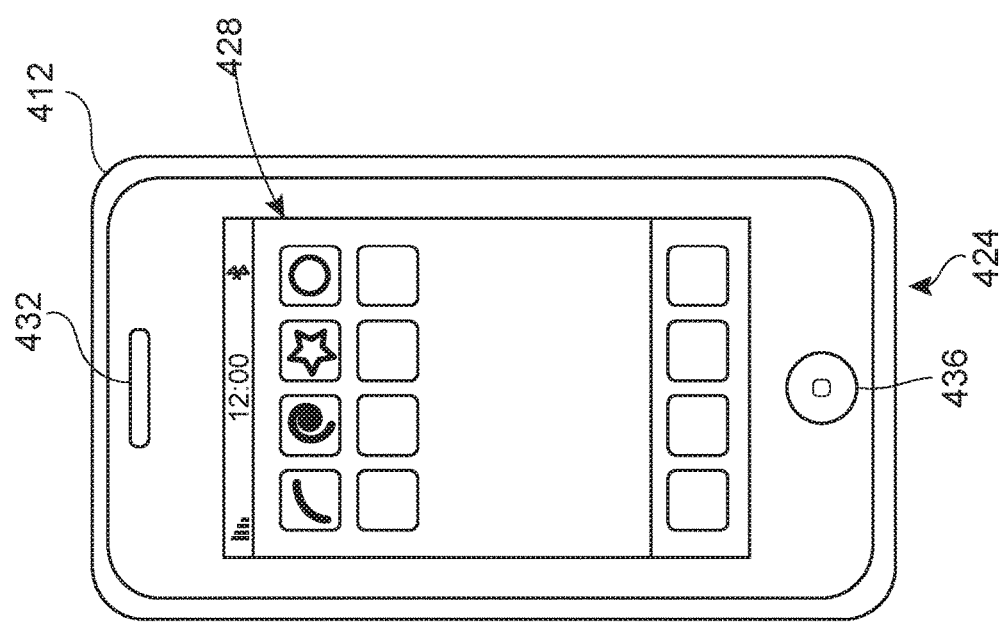
FIG. 41 is a plan view of an exemplary mobile device for use in combination with certain preferred embodiments.
Figure 43:
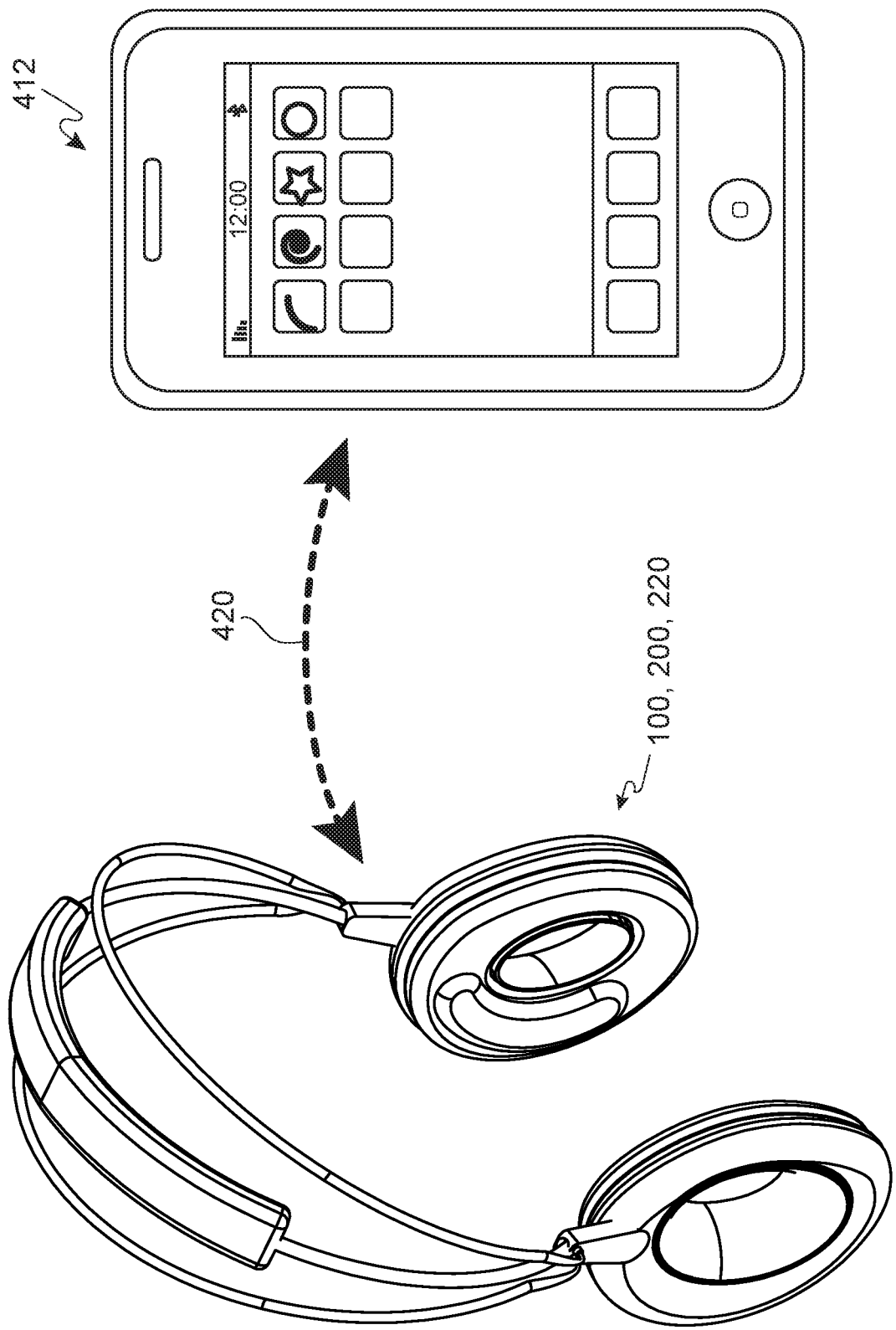
FIG. 43 illustrates communication between an exemplary mobile device and an exemplary therapeutic device.

FIGS. 41-43 illustrate an exemplary mobile device platform+software package for interface with embodiments of cooling device(s). For this, a mobile phone 412, with an integrated software application 416, may be structured to communicate (wirelessly or wired) 420 with a cooling device. The communication is desirably 2-way: the cooling device sends/receives data from the mobile device, and the mobile device sends/receives data from the cooling device. Advantageously, a mobile phone includes: a microphone 424; a user interface 428 to convey information to a user; a speaker 432; and a user input control including button 436 to receive input from a user.

An exemplary mobile device platform generally indicated at 412 in FIG. 42 desirably includes: one or more software application(s) 416; a touch screen user input control 436; a microprocessor 440; on-board memory 444; a system microphone 448; an audio codec 452 to compress/decompress audio data; mobile device/cellular network communication circuitry 456; GPS transceiver module 460; wide/local area network (WLAN) transceiver module 464; Bluetooth transceiver 468; GPS antenna 472; WLAN antenna 476; Bluetooth antenna 480; and cellular antenna 484. As indicated generally in FIG. 43, a mobile platform may be placed in cooperation with a therapy device (e.g., passive or active) to monitor, detect, and provide therapy responsive to a perceived sonic event.

While aspects of the invention have been described in particular with reference to certain illustrated embodiments, such is not intended to limit the scope of the invention. The present invention may be embodied in other specific forms without departing from its spirit or essential characteristics. For one example, one or more element may be extracted from one described or illustrated embodiment and used separately or in combination with one or more element extracted from one or more other described or illustrated embodiment(s), or in combination with other known structure. The described embodiments are to be considered as illustrative and not restrictive. Obvious changes within the capability of one of ordinary skill are encompassed within the present invention.

The scope of the invention for which a monopoly position is currently desired is indicated by the appended claims rather than by the foregoing description. All changes which come within the meaning and range of equivalency of the claims are to be embraced within their scope.

What is claimed is:

1. An apparatus, comprising:
a thermal therapy device structured to interface in installed registration with an ear of a human head, the device being structured to place a heat transfer contact element in contact with the head at a localized area, the localized area extending only partially around a circumference of the ear;
a resilient element configured to be biased, due to bending from a neutral, non-biased configuration, to urge the contact element toward contact with the head, wherein:
the device is structured to maintain an open pathway from the local environment to the ear canal of the ear on which the device is installed; and
the open pathway passes through a tunnel in the device, the tunnel being structured to provide line-of-sight into the canal, further comprising:
a mobile platform in operable cooperation with the device to monitor, detect, and/or provide therapy responsive to a perceived sonic event.

2. The apparatus according to claim 1, wherein:
the device is structured to maintain a portion of the heat contact element at a posterior position with respect to the ear canal of the ear on which the device is installed.

3. The apparatus according to claim 2, further comprising:
an ear opening structured to cause radial compression against an exterior surface of the ear, the opening being structured to receive an ear in penetration there-through during installation of the device on the head.

4. The apparatus according to claim 3, wherein:
the ear opening is generally ovaloid at a neutral, unbiased configuration, the ear opening to generate a torque against a top and a bottom of an ear to resist twisting of the device about an axis perpendicular to the head.

5. The apparatus according to claim 3, wherein:
the ear opening extends around an entire circumference of an installed ear.

6. The apparatus according to claim 1, wherein:
the device is passive.

7. The apparatus according to claim 1, wherein:
the device comprises an electrically active thermal element.

8. The apparatus according to claim 1, further comprising:
a contact cavity and a bulk cavity carried by the device to displace in accordance with motion of the head of a user of the device, each of the contact cavity and the bulk cavity carrying a heat transferring substance, the bulk cavity being disposed in thermal communication with the contact cavity, and wherein:
a portion of the contact cavity forms the contact element.

9. The apparatus according to claim 1, wherein:
the device is operably affixed to a helmet.

10. An apparatus, comprising:
a thermal therapy device structured to interface in installed registration with an ear of a human head, the device being structured to place a heat transfer contact element in contact with the head at a localized area, the localized area extending only partially around a circumference of the ear;
the device being structured to maintain a portion of the heat contact element at a posterior position with respect to the ear canal of the ear on which the device is installed; and
an ear opening structured to cause radial compression against an exterior surface of the ear, the opening being structured to receive an ear in penetration there-through during installation of the device on the head; wherein:
the ear opening comprises an ear cone affixed to the therapy device at a large diameter open end of the cone to dispose a free-standing conic element that extends to a smaller diameter opening disposed at the opposite end of the ear cone.

11. The apparatus according to claim 10, wherein:
an internal conic surface of the ear cone is structured to stretch and accommodate in compression against an exterior surface of an installed ear.

* * * * *